United States Patent
Ertl (12)

(10) Patent No.: US 6,210,663 B1
(45) Date of Patent: Apr. 3, 2001

(54) METHODS OF AUGMENTING MUCOSAL IMMUNITY THROUGH SYSTEMIC PRIMING AND MUCOSAL BOOSTING

(75) Inventor: Hildegund C. J. Ertl, Villanova, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/377,579

(22) Filed: Aug. 19, 1999

Related U.S. Application Data

(60) Provisional application No. 60/097,185, filed on Aug. 20, 1998.

(51) Int. Cl.$^7$ ........................... A01N 63/00; A01N 43/04; A61K 39/21; A61K 39/27; C12N 15/00
(52) U.S. Cl. .................. 424/93.2; 424/184.1; 424/208.1; 424/229.1; 424/249.1; 435/320.1
(58) Field of Search .............................. 424/224.1, 184.1, 424/73.2, 249.1, 208.1, 229.1; 435/69.1, 320.1; 514/44

(56) References Cited

U.S. PATENT DOCUMENTS

| | | | |
|---|---|---|---|
| 4,393,201 | 7/1983 | Curtis et al. | 536/23.5 |
| 5,698,202 | * 12/1997 | Ertl et al. | 424/199.1 |

OTHER PUBLICATIONS

Whittle et al. J. Med. Microbiol. 46:1029–1038, Dec. 1997.*
Sasaki et al. Journal of Virology. 72(6): 4931–9, Jun. 1998.*
Natuk et al. Dev Biol Standard. 82: 71–7, 1994.*
Robinson, HL. Vaccine. 15(8): 785–787, Jun. 1997.*
Staats et al. Cur Opin Immunology. 6: 572–583, Aug. 1994.*
McCluskie et al. Molecular Medicine. 287–300, May 1999.*
Barnett et al. J Neuroimmunology. 64: 163–173, Dec. 1997.*
J. J. Kim, "Development of a Multicomponent Candidate Vaccine for HIV–1," *Vaccine*, 15 (8):879 (Jun. 1997).
S.W. Barnett et al., "Vaccination with HIV–1 gp 120 DNA Induces Immune Responses that are Boosted by a Recombinant gp120 Protein Subunit," *Vaccine*, 15(80):869–873 (Jun. 1997).
N.L. Letvin et al., "Potent, Protective anti–HIV Immune Responses Generated by Binodal HIV Envelope DNA Plus Protein Vaccination," *Proc. Natl. Acad. Sci., USA*, 94:9378–9383 (Aug. 1997).
R.A. Gramzinski et al., "Immune Response to a Hepatitis B DNA Vaccine in *Aotus* Monkeys: A Comparison of Vaccine Formulation, Route, and Method of Administration," *Molecular Med.*, 4:109–118 (Feb. 1998).
Z. Xiang and H. Ertl, "Induction of Mucosal Immunity with a Replication–Defective Adenoviral Recombinant," *Vaccine*, 17:2003–2008 (Apr. 9, 1999).

Z. Xiang et al., "Induction of Genital Immunity by DNA Priming and Intranasal Booster Immunization with a Replication–Defective Adenoviral Recombinant," *J. Immunol.*, 6716 (Jun. 1, 1999).
J. Schneider et al., "Enhanced Immunogenicity for CD9+ T Cell Induction and Complete Protective Efficacy of Malaria DNA Vaccination by Boosting with Modified Vaccinia Virus Ankara," *Nature Med.*, 4:397 (Apr. 1998).
M. Sedeguh et al., "Boosting with Recombinant Vaccinia Increases Immunogenicity and Protective Efficacy of Malaria DNA Vaccine," *Proc. Natl. Acad. Sci., USA*, 95:7648 (Jun. 1998).
Database Medline on PubMed, The Wistar Institute, (Philadelphia, PA, USA), PMID: 10217600, UI: 99231952, Xiang et al., "Induction of Mucosal Immunity with a Replication–Defective Adenoviral Recombinant", Abstract, *Vaccine* (Apr. 9, 1999).
Database Medline on PubMed, The Wistar Institute, (Philadelphia, PA, USA), PMID: 10352290, UI:99282958, Xiang et al., "Induction of Genital Immunity by DNA Priming and Intranasal Booster Immunization with a Replication–Defective Adenoviral Recombinant", Abstract, *J. Immunol.* (Jun. 1, 1999).
Staats et al., "Mucosal Immunity to Infection with Implications for Vaccine Development", *Curr. Opin. Immunol.*, 6:572–583 (Aug. 1994).
Holmgren et al., "Mucosal Immunity: Implications for Vaccine Development," *Immunobiol.*, 184:157–179 (Feb. 1992).
Hopkins et al., "A Recombinant Salmonella typhimurium Vaccine induces Local Immunity by Four Different Routes of Immunization," *Infect. Immun.*, 63:3279–3286 (Sep. 1995).

(List continued on next page.)

*Primary Examiner*—Deborah J. R. Clark
*Assistant Examiner*—Carrie Stroup
(74) *Attorney, Agent, or Firm*—Howson and Howson

(57) ABSTRACT

A method for inducing and enhancing mammalian mucosal immunity includes the steps of first administering to a mammal via a non-mucosal route a suitable amount of a priming vaccine composition which comprises a DNA sequence encoding an antigen of a pathogen under the control of regulatory sequences directing expression thereof in a mammalian cell, and subsequently, administering intranasally a boosting vaccine composition which comprises the same antigen in protein form or a DNA sequence encoding the same antigen. A method to reduce the anti-viral immune response to a recombinant viral vaccine includes the steps of administering a similar priming DNA vaccine composition that lacks any viral protein and subsequently administering as a boosting vaccine, a recombinant virus containing a DNA sequence encoding the same antigen as encoded by the DNA vaccine, wherein upon said recombinant virus vaccine administration, the immune response to the antigen is enhanced and the immune response to the recombinant virus is reduced.

13 Claims, 10 Drawing Sheets

OTHER PUBLICATIONS

Wu and Russell, "Induction of Mucosal Immunity by Intranasal Application of a Streptococcal Surface Protein Antigen with the Cholera Toxin B Subunit," *Infect. Immun.,* 61:314–322 (Jan. 1993).

Staats et al., "Systemic and Vaginal Antibody Responses After Intranasal Immunization with the HIV–1 C4/V3 Peptide T1SP10 MN(A)," *J. Immunol.,* 157:462–472 (Jul. 1, 1996).

Gallichan and Rosenthal, "Specific Secretory Immune Responses in the Female Genital Tract Following Intranasal Immunization with a Recombinant Adenovirus Expressing Glycoprotein V of Herpes Simplex Virus," *Vaccine,* 13:1589–1595 (Nov. 1995).

Lehner et al., "Protective Mucosal Immunity Elicited by Targeted Iliac Lymph Node Immunization with a Subunit SIV Envelope and Core Vaccine Macaques," *Nature Med.,* 2:767–775 (Jul. 1996).

Yang et al., "Cellular and Humoral Immune Responses to Viral Antigens Create Barriers to Lung–Directed Gene Therapy with Recombinant Adenoviruses," *J. Virol.,* 69:2004–2015 (Apr. 1995).

Yang et al., "Immune Responses to Viral Antigens Versus Transgene Product in the Elimination of Recombinant Adenovirus–Infected Heptaocytes in Vivo," *Gene Therapy,* 3:137–144 (1995).

Kuklin et al., "Induction of Mucosal Immunity Against Herpes Simplex Virus by Plasmid DNA Immunization," *J. Virol.,* 71:3138–3145 (Apr. 1997).

Xu–Amano et al., "Helper T Cell Subsets for Immunoglobulin A Response: Oral Immunization with Tetanus Toxoid and Cholera toxin as Adjuvant Selectively Induces Th2 Cells in Mucosa Associated Tissues," *J. Exp. Med.,* 178:1309–1320 (Oct. 1993).

Fujihashi, "$\gamma/\beta$Cell–Deficient Mice have Impaired Mucosal Immunoglobulin A Responses," *J. Exp. Med.,* 183:1929–1935 (Apr. 1996).

* cited by examiner

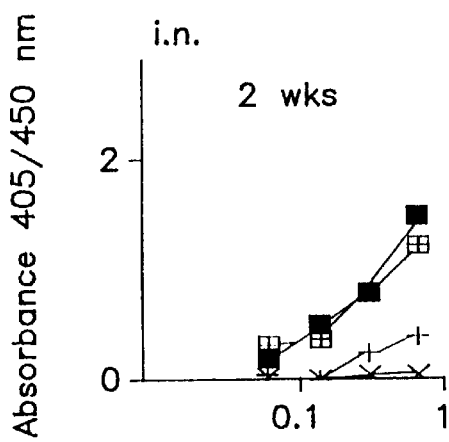
FIG. IA
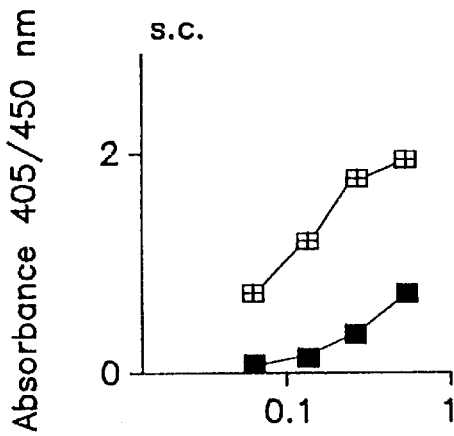
FIG. IB
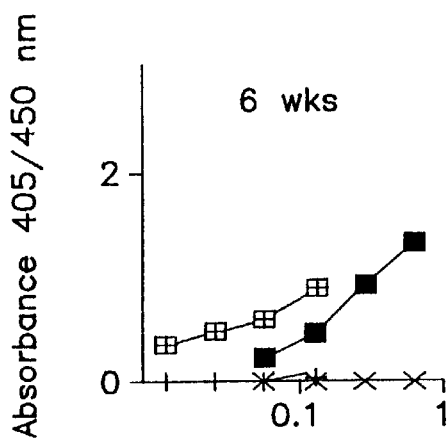
FIG. IC
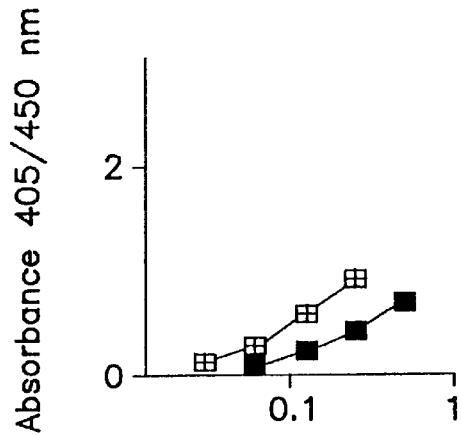
FIG. ID

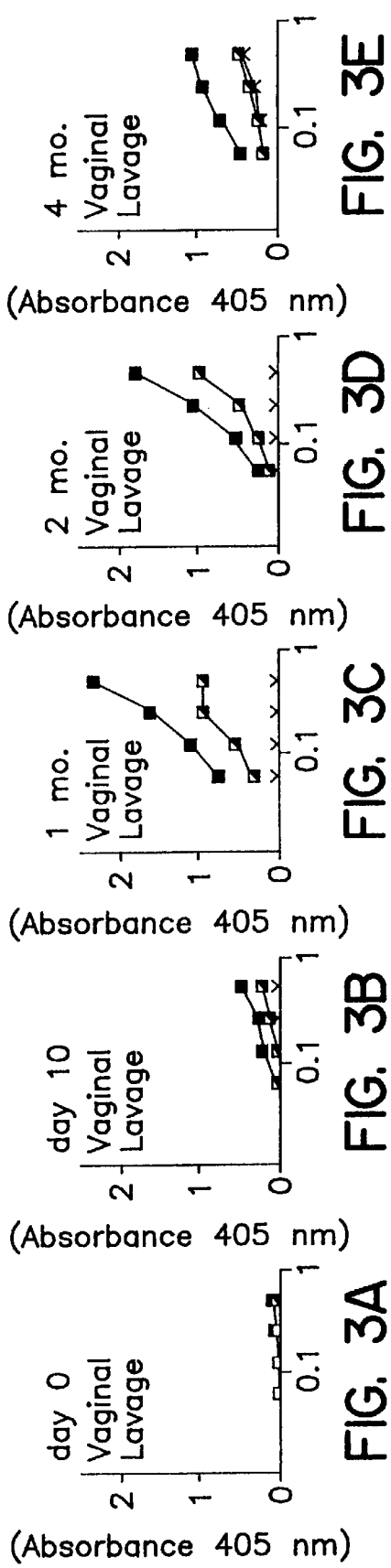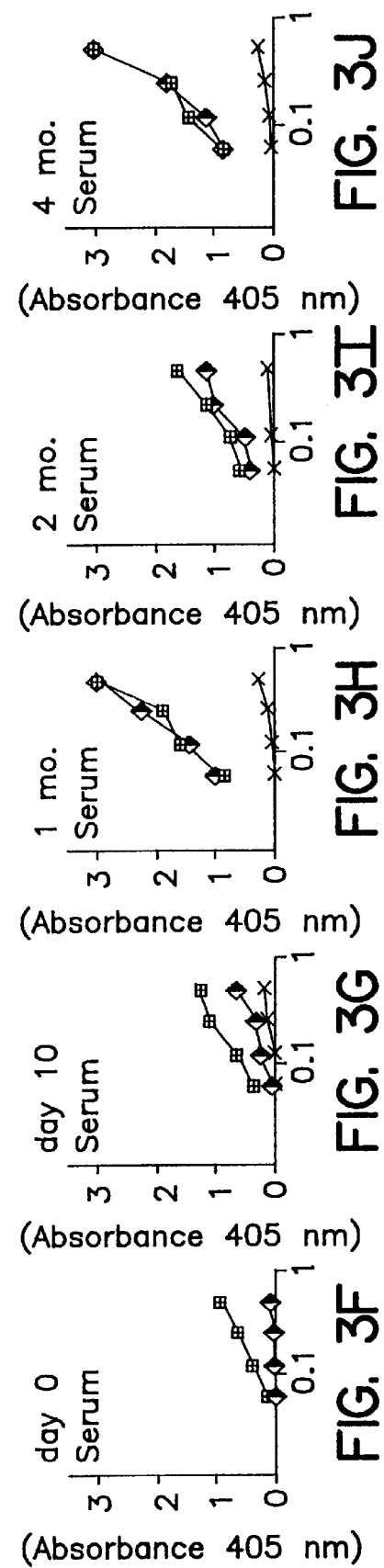

METHODS OF AUGMENTING MUCOSAL IMMUNITY THROUGH SYSTEMIC PRIMING AND MUCOSAL BOOSTING

CROSS-REFERENCE TO OTHER APPLICATIONS

This application claims the benefit of the priority of U.S. provisional application No. 60/097,185, filed Aug. 20, 1998.

GOVERNMENT SUPPORT

This invention was supported in part by funds from the U.S. Government National Institutes of Health Grants No. SR01-AI 33683 and No. SR01-AI 37166). The U.S. Government may therefore have certain rights in the invention.

FIELD OF THE INVENTION

The field of the invention is modulation of mucosal immunity using systemic and mucosal immunization techniques.

BACKGROUND OF THE INVENTION

The human immune system may be broadly subdivided into two separate, interacting subsystems. The central immune system patrols the inner organs and tissues; and the mucosal immune system provides a defensive barrier against microbes that enter the body through the surfaces of the airways, intestines and urogenital tract. While the central immune system has been the subject of intensive study over the last three decades, knowledge of the mucosal immune system, which in humans covers a surface area of approximately 400 $m^2$ and is therefore by far the larger of the two systems, remains poor.

Intranasal immunization of a variety of vaccine compositions has been reported to favor the development of B cell responses at distal mucosal sites, for example, resulting in vaginal antibody secretion. Among such vaccines are: a recombinant *Salmonella typhimurium* vaccine expressing a hepatitis virus antigen [Hopkins et al, *Infect. Immun.*, 6:3279–3286 (1995)], a streptococcal surface antigen coupled to the cholera toxin (CT) B subunit [Wu and Russell, *Infect. Immun.*, 61:314–322 (1993)], an HIV peptide given with CT [Staats et al., *J. Immunol.*, 1:462–472 (1996)], a replication competent adenoviral recombinant expressing a herpes virus antigen [Gallichan and Rosenthal, *Vaccine*, 13:1589–1595 (1995)], and a DNA vaccine with CT as an adjuvant [Kuklin et al., *J. Virol.*, 21:3138–3145 (1997)]. However, the limited understanding of the mucosal immune system has hampered the development of efficacious vaccines to numerous important human pathogens which infect the host via the genital tract mucosal surface. Despite the above reports, vaccines which induce effective mucosal immunity, particularly vaccines to induce protective immunity against sexually transmitted pathogens, which infect humans via the mucosa and which constitute major emerging and re-emerging infectious diseases, are not currently available.

Such agents include human immunodeficiency virus (HIV), human papilloma viruses (HPV), *Neisseria gonorrhea, Treponema pallidum,* and herpes simplex virus types 1 and 2 (HSV-1 and HSV-2). These agents often establish persistent infections once they have avoided the mucosal barrier. Further, systemic immunization capable of protecting against a systemic infection may not protect against a mucosal infection [Lehner et al., *Nature Med.*, 2:767–775 (1996)]. Accordingly, systemic immunization represents a secondary (and possibly ineffective) means of defense once the first line of defense, i.e., mucosal immunity, has been breached.

Vaccine compositions which have been administered systemically or mucosally include adenovirus constructs that express reporter proteins, upon either intravenous inoculation targeting the liver or upon intratracheal application targeting the lung. However, a strong neutralizing antibody response to the adenoviral antigens of the recombinant adenovirus often reduces the rate of infection upon a second application of such recombinant adenovirus as a vaccine construct. These vaccine constructs induce CD8+ T cells reactive to both the reporter transgene protein product and to the viral antigens of the adenoviral construct. This immune response causes clearance of recombinant adenovirus-infected cells from the animal within 10–14 days post-inoculation [Yang et al., 1995, *J. Virol.*, 69:2004–2015; Yang et al., 1995, *Gene Therapy*, 3:137–144]. Adenoviral recombinants also stimulate CD4+ T helper cells, predominantly of the Th1 type. These T helper cells promote activation of an antibody response which prevents efficacious re-infection upon a second application of the adenoviral vaccine vehicle. Accordingly, the strong immune response to the adenovirus vaccine vehicle curtails the necessary secondary immune response to the antigen product expressed by the recombinant vaccine upon booster immunization.

In order to circumvent this limitation of adenoviral recombinant vectors, genetic vaccines based on plasmid vectors have been tested for their ability to induce a protective immune response in animals. In this regard, prior studies have demonstrated that plasmid-based vaccines, upon systemic application, prime the systemic immune system to a second systemic immunization with a traditional antigen, such as a protein or a recombinant virus [Xiang et al, *Springer Semin. Immunopathol.*, 19:257–268 (1997); J. Schneider et al, *Nature Med.*, 4:397 (1998); M. Sedeguh et al., *Proc. Natl. Acad. Sci., USA;* 95:7648 (1998)]. However, these plasmid-based vaccines appear to induce only low levels of genital IgA secretion upon co-administration with cholera toxin [Kuklin et al., *J. Virol.*, 71:3138–3145 (1997)]. Therefore, plasmid-based vaccines, while useful for inducing a systemic immune response, may not be adequate for the purposes of generating a protective mucosal immune response.

There is a long-felt and acute need for the design and development of efficacious vaccines to induce or confer mucosal immunity in humans to human pathogens. The present invention satisfies this need.

SUMMARY OF THE INVENTION

In one aspect, the invention relates to a method of inducing mammalian mucosal immunity to a pathogen. The method includes the steps of:

(a) administering via a non-mucosal route of administration an effective amount of a priming DNA vaccine composition which comprises a DNA sequence encoding an antigen of the pathogen. This DNA vaccine may be simply the DNA encoding the antigen, the DNA encoding the antigen under the control of regulatory sequences directing expression thereof in a mammalian cell, or such DNA sequences in a plasmid or vector containing other nucleotide sequences; and (b) subsequently administering intranasally to the mammal an effective amount of a boosting vaccine composition which comprises the antigen in protein form, fragments thereof, a DNA sequence encoding the antigen, and optionally under the control of a regulatory sequence directing expression thereof in a mammalian cell, or a bacterial or viral carrier comprising the DNA sequence encoding the antigen.

In another aspect, the invention provides a method of reducing the unwanted immune response to a recombinant vaccine vehicle or carrier. A priming DNA vaccine composition is administered, which comprises a DNA sequence encoding an antigen of a pathogen under the optional control of regulatory sequences directing expression thereof in a mammalian cell. Significantly, this DNA vaccine contains no sequences encoding antigenic proteins or peptides of the vaccine vehicle outside of the antigen-encoding and regulatory sequences. This DNA vaccine is administered prior to administering a recombinant vaccine vehicle. The recombinant vaccine composition comprises a recombinant virus or bacteria encoding a DNA sequence encoding the same antigen under the control of a regulatory sequence directing expression of the antigen in a mammalian cell or tissue. Upon administration of the recombinant vaccine, the immune response to the antigen is enhanced and the immune response to the recombinant vehicle is reduced.

In still another aspect, this invention provides a kit for inducing mucosal immunity in mammals. This kit contains the priming DNA vaccine composition described above; a boosting vaccine composition described above; as well as instructions for the use of the kit. In another embodiment, the kit comprises a co-priming amount of a genetic adjuvant. In still another embodiment, the kit contains an applicator for delivering the priming composition to the mammal via a non-mucosal route, and/or an applicator for delivering the boosting composition to the mammal mucosally, preferably intranasally.

BRIEF DESCRIPTION OF THE DRAWINGS

FIG. 1A is a graph depicting the presence of antibody titers, measured by absorbance at 405 or 450 nm, to rabies virus antigens in the sera and vaginal lavage obtained from female C3H/He mice. One experimental group of mice (immune) was given a single intranasal (i.n.) immunization of $2 \times 10^6$ plaque-forming units (pfu) of Adrab.gp recombinant adenovirus. Naive, non-immunized mice formed the control group. Sera and vaginal lavage were harvested from the mice at 2 weeks after vaccination. The symbols are as follows: immune sera (⊞); control sera (+); immune vaginal lavage (■); control vaginal lavage (X).

FIG. 1B is a graph depicting the presence of antibody titers to rabies virus antigens in the sera and vaginal lavage obtained from female C3H/He mice. One experimental group of mice (immune) was given a single subcutaneous (s.c.) immunization of $2 \times 10^6$ plaque-forming units (pfu) of Adrab.gp recombinant adenovirus. Sera and vaginal lavage were harvested from the mice at 2 weeks after vaccination. The symbols are as follows: immune sera (⊞); and immune vaginal lavage (■). The controls were the same as those in FIG. 1A.

FIG. 1C is a graph depicting the antibody titers of sera and vaginal lavage harvested from the mice of FIG. 1A at 6 weeks after vaccination. The symbols are the same as in FIG. 1A. The results for the 6 week control samples were comparable to that of the 2 week sample of FIG. 1A, and are not shown.

FIG. 1D is a graph depicting the antibody titers of sera and vaginal lavage harvested from the mice of FIG. 1B at 6 weeks after vaccination. The symbols are the same as in FIG. 1B. The controls were the same as in FIG. 1C.

FIG. 3A is a graph depicting the antibody titers (measured at absorbance 405 nm) to rabies virus in the vaginal lavage of mice primed with an intramuscular (i.m.) injection of either 40 μg of pVRrab.gp vector (■), or 40 μg of empty pVR1012.2 cloning vector (⊞). Four months later, on day 0, the mice were boosted i.n. with 2×10⁶ pfu of Adrab.gp virus. This graph is the harvested lavage just before boosting on day 0. Vaginal lavage from naive mice were tested for comparison (X).

FIG. 3B is a graph depicting the vaginal lavage antibody titers of the mice of FIG. 3A in lavage harvested 10 days after boosting. The symbols are the same as in FIG. 3A.

FIG. 3C is a graph depicting the vaginal lavage antibody titers of the mice of FIG. 3A in lavage harvested one month after boosting. The symbols are the same as in FIG. 3A.

FIG. 3D is a graph depicting the vaginal lavage antibody titers of the mice of FIG. 3A in lavage harvested two months after boosting. The symbols are the same as in FIG. 3A.

FIG. 3E is a graph depicting the vaginal lavage antibody titers of the mice of FIG. 3A in lavage harvested four months after boosting. The symbols are the same as in FIG. 3A.

FIG. 3F is the graph depicting the serum antibody titers (measured at absorbance 405 nm) to rabies virus of the mice of FIG. 3A. Sera were harvested just prior to boost from mice primed with the pVRrab.gp vector (⊞); and mice primed with empty pVR1012.2 cloning vector (◆). Serum from naive mice were tested for comparison (X).

FIG. 3G is the graph depicting the serum antibody titers of the mice of FIG. 3B, with the symbols as in FIG. 3F.

FIG. 3H is the graph depicting the serum antibody titers of the mice of FIG. 3C, with the symbols as in FIG. 3F.

FIG. 3I is the graph depicting the serum antibody titers of the mice of FIG. 3D, with the symbols as in FIG. 3F.

FIG. 3J is the graph depicting the serum antibody titers of the mice of FIG. 3E, with the symbols as in FIG. 3F.

DETAILED DESCRIPTION OF THE INVENTION

Figure 1E:
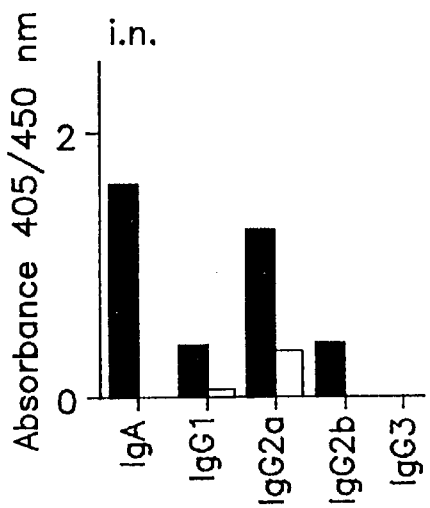
FIG. 1E is a bar graph reporting on the antibody isotype profile of the sera and vaginal lavage of the mice of FIG. 1A. The abbreviations are as follows: immune vaginal lavage (■); control vaginal lavage (▨) ; and immune serum (□).
Figure 1F:
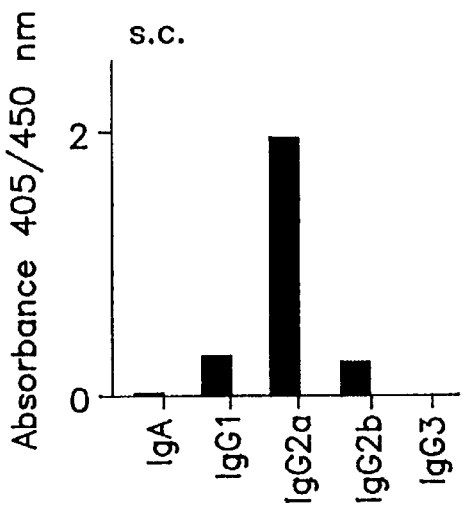
FIG. 1F is a bar graph reporting on the antibody isotype profile of the sera and vaginal lavage of the mice of FIG. 1B. The abbreviations are the same as in FIG. 1E.
Figure 1G:
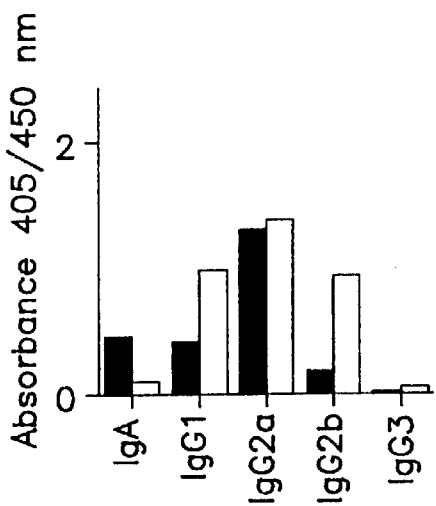
FIG. 1G is a bar graph reporting on the antibody isotype profile of the sera and vaginal lavage of the mice of FIG. 1C. The abbreviations are the same as in FIG. 1E. Data on the isotypes present in control sera are only shown for the 6 week sample.
Figure 1H:
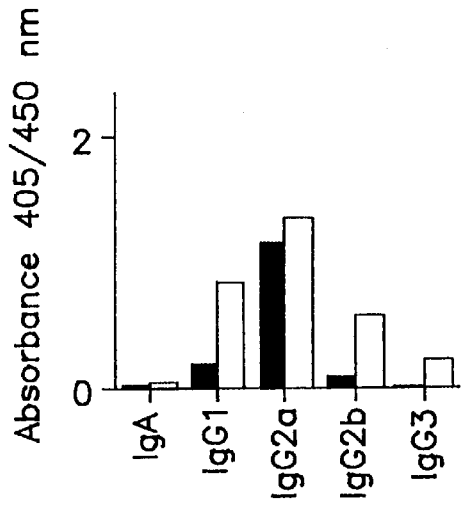
FIG. 1H is a bar graph reporting on the antibody isotype profile of the sera and vaginal lavage of the mice of FIG. 1D. The abbreviations are the same as in FIG. 1E. Data on the isotypes present in control sera are only shown for the 6 week sample.
Figure 2A:
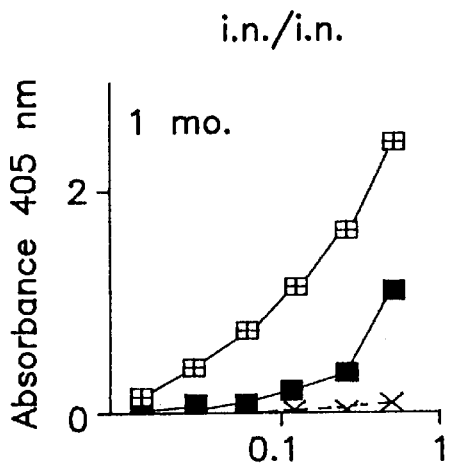
FIG. 2A is a graph depicting the antibody response (absorbance 405 nm) to rabies virus in sera and vaginal lavage of female C3H/He mice after an intranasal immunization of $2 \times 10^6$ pfu with the Adrab.gp recombinant vaccine, followed by a boost of the same dosage of Adrab.gp i.n. The antirabies virus antibody titers of immune sera (⊞), immune vaginal lavage (■), and sera of naive control mice (X), were measured at 1 month after boosting.
Figure 2D:
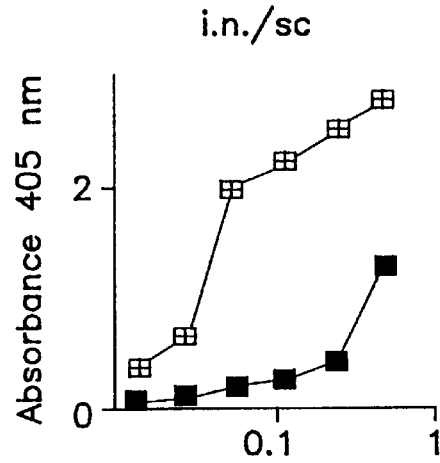
FIG. 2D is a graph depicting the antibody response (absorbance 405 nm) to rabies virus in sera and vaginal lavage of female C3H/He mice after an intranasal immunization of $2 \times 10^6$ pfu with the Adrab.gp recombinant vaccine, followed by a boost of the same dosage of Adrab.gp s.c. The antirabies virus antibody titers of immune sera (⊞), and immune vaginal lavage (■) were measured one month after boosting.
Figure 2B:
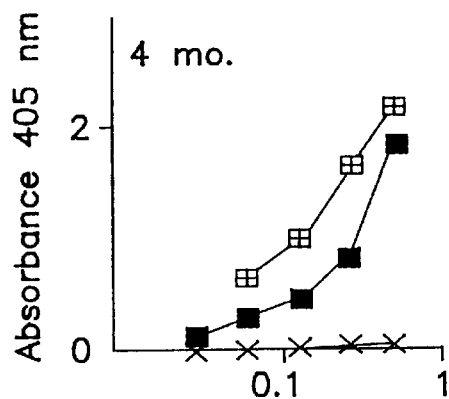
FIG. 2B is a graph depicting the results of the mice of FIG. 2A four months after boosting.
Figure 2E:
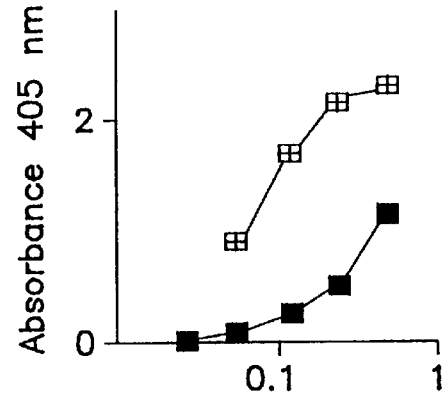
FIG. 2E is a graph depicting results of the mice of FIG. 2D four months after boosting.
Figure 2C:
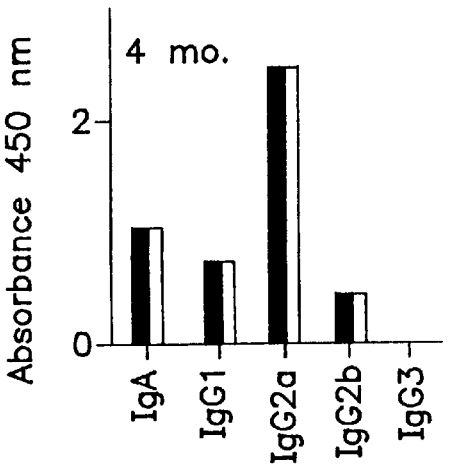
FIG. 2C is a bar graph reporting on the antibody isotype profile (absorbance 450 nm) of the vaginal lavage of the mice of FIG. 2A tested at four months after boosting to determine the isotypes of the antibodies to rabies virus. A control vaginal lavage sample from naive mice was tested for comparison. This sample was negative (OD±0.02).
Figure 2F:
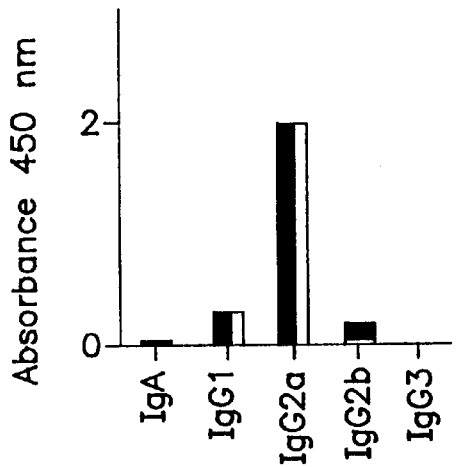
FIG. 2F is a bar graph reporting on the antibody isotype profile (absorbance 450 nm) of the vaginal lavage of the mice of FIG. 2D tested at four months after boosting to determine the isotypes of the antibodies to rabies virus. A control vaginal lavage sample from naive mice was tested for comparison. This sample was negative (OD±0.02).
Figure 2G:
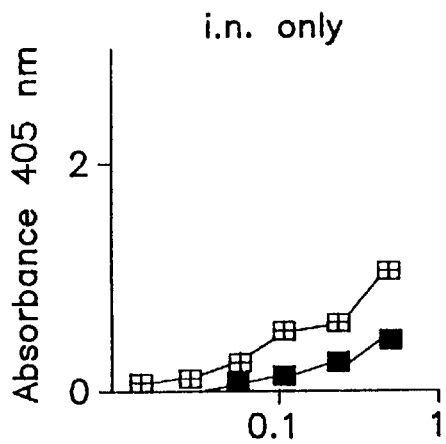
FIG. 2G is a graph depicting the antibody response (absorbance 405 nm) to rabies virus in sera and vaginal lavage of female C3H/He mice after a single intranasal immunization of $2 \times 10^6$ pfu with the Adrab.gp recombinant vaccine. The antirabies virus antibody titers of immune sera (⊞) and immune vaginal lavage (■) were measured one month after immunization.
Figure 2H:
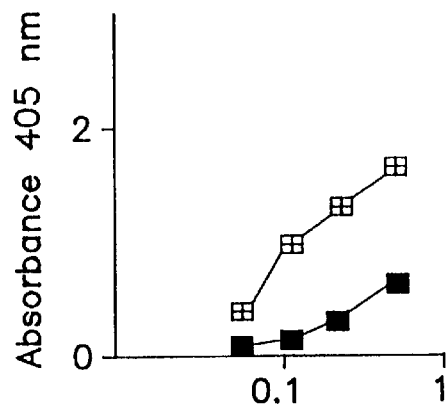
FIG. 2H is a graph depicting the results of the mice of FIG. 2G four months after immunization.
Figure 2I:
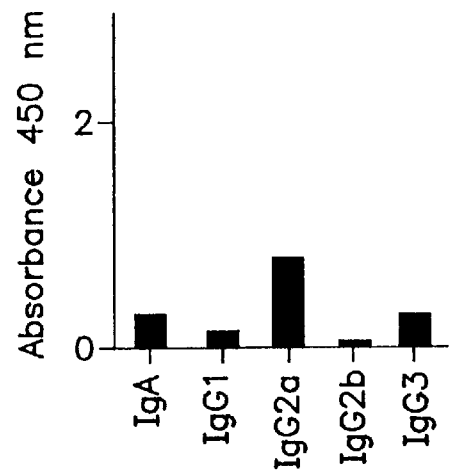
FIG. 2I is a bar graph reporting on the antibody isotype profile (absorbance 450 nm) of the vaginal lavage of the mice of FIG. 2G tested at four months after immunization to determine the isotypes of the antibodies to rabies virus. A control vaginal lavage sample from naive mice was tested for comparison. This sample was negative (OD±0.02).
Figure 3K:
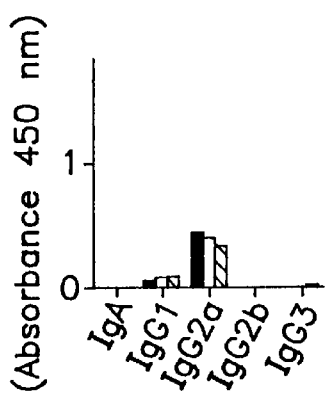
FIG. 3K is a bar graph depicting the antibody isotypes (measured at absorbance 450 nm) of the vaginal lavage samples of FIG. 3A. The abbreviations used are as follows: Vaginal lavage obtained from pVRrab.gp-primed (■); pVR1012.2-primed (□); and naive mice (▨).
Figure 3L:
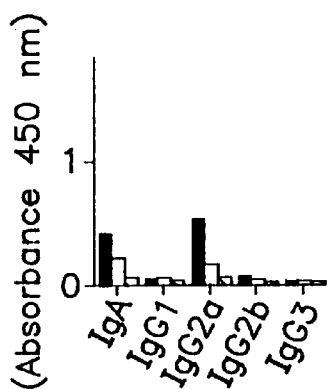
FIG. 3L is a bar graph depicting the antibody isotypes (measured at absorbance 450 nm) of the vaginal lavage samples of FIG. 3B using the symbols of FIG. 3K.
Figure 3M:
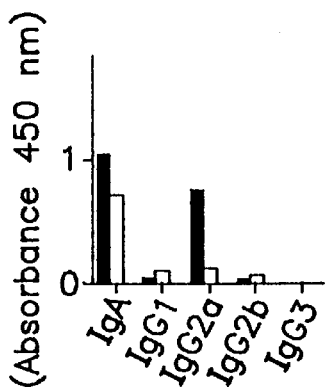
FIG. 3M is a bar graph depicting the antibody isotypes (measured at absorbance 450 nm) of the vaginal lavage samples of FIG. 3C using the symbols of FIG. 3K.
Figure 3N:
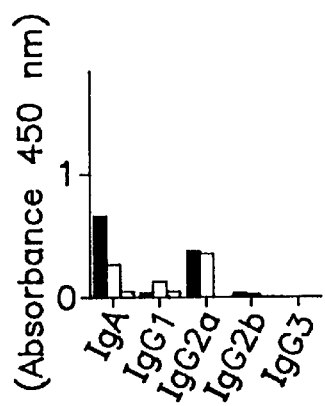
FIG. 3N is a bar graph depicting the antibody isotypes (measured at absorbance 450 nm) of the vaginal lavage samples of FIG. 3D using the symbols of FIG. 3K.
Figure 3O:
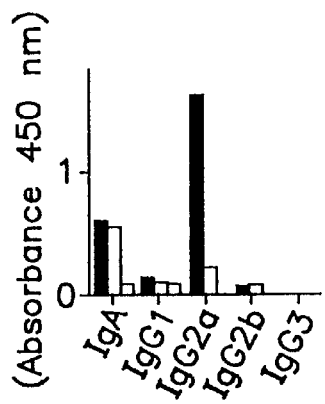
FIG. 3O is a bar graph depicting the antibody isotypes (measured at absorbance 450 nm) of the vaginal lavage samples of FIG. 3E using the symbols of FIG. 3K.
Figure 3P:
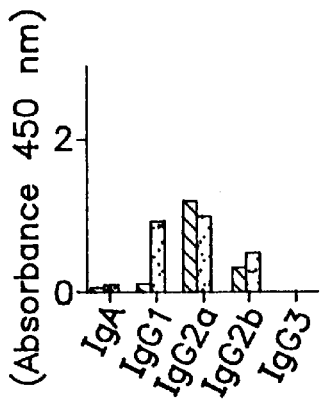
FIG. 3P is a bar graph depicting the antibody isotypes (measured at absorbance 450 nm) of the sera samples of FIG. 3H. The abbreviations used are as follows: Serum obtained from pVRrab.gp-primed (▨); pVR1012.2-primed (▨); and naive mice (□).
Figure 3Q:
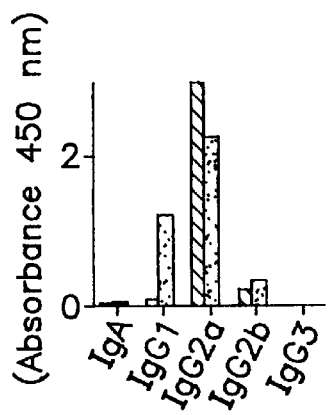
FIG. 3Q is a bar graph depicting the antibody isotypes (measured at absorbance 450 nm) of the sera samples of FIG. 3I using the symbols of FIG. 3Q.
Figure 3R:
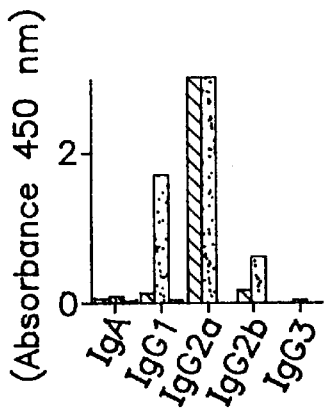
FIG. 3R is a bar graph depicting the antibody isotypes (measured at absorbance 450 nm) of the sera samples of FIG. 3J using the symbols of FIG. 3Q.
Figure 4A:
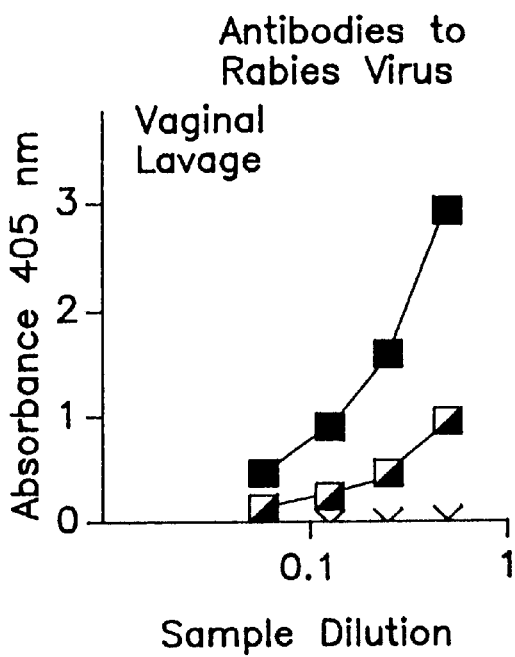
FIG. 4A is a graph depicting antibodies to rabies virus measured in vaginal lavage (at 405 nm) of mice primed i.m. with 50 μg of the pSG5rab.gp vector or empty pSG5 vector and boosted 6 weeks later with 2×10⁶ pfu of Adrab.gp virus given i.n. The symbols are: naive mice (X); pSG5 empty vector-primed mice (▲); and pSG5rab.gp-primed mice (■).
Figure 4B:
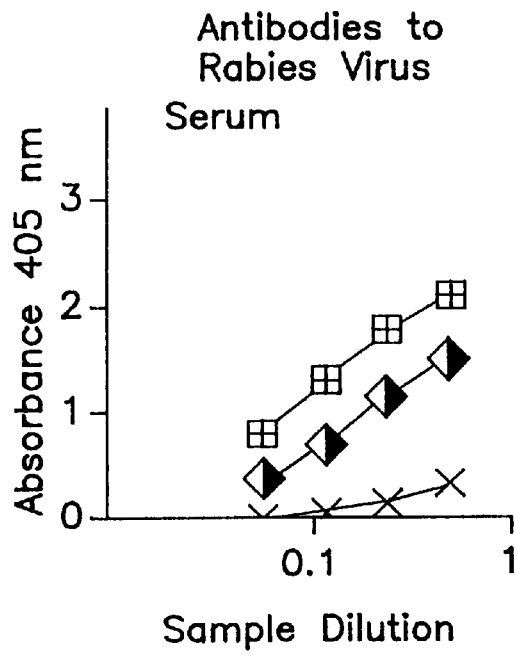
FIG. 4B is a graph depicting antibodies to rabies virus measured in serum (at 405 nm) of mice of FIG. 4A. The symbols are: naive mice (X); pSG5 empty vector-primed mice (◆); and pSG5rab.gp-primed mice (⊞).
Figure 4C:
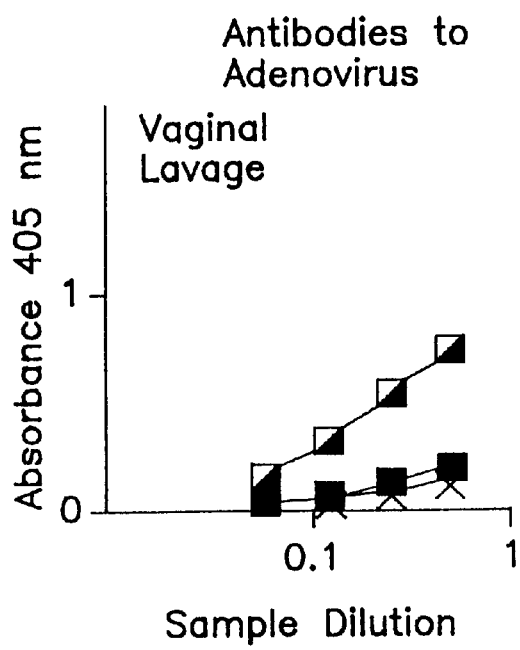
FIG. 4C is a graph depicting antibodies to adenovirus measured in vaginal lavage (at 405 nm) of the mice of FIG. 4A. The symbols are: naive mice (X); pSG5 empty vector-primed mice (▲); and pSG5rab.gp-primed mice (■).
Figure 4D:
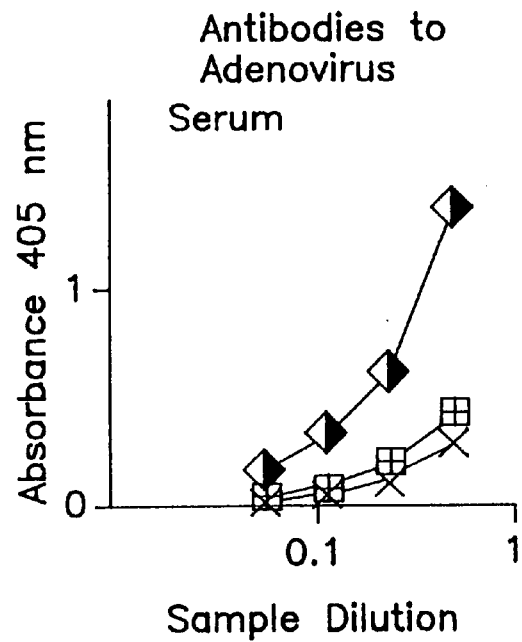
FIG. 4D is a graph depicting antibodies to adenovirus measured in serum (at 405 nm) of mice of FIG. 4B. The symbols are: naive mice (X); pSG5 empty vector-primed mice (◆); and pSG5rab.gp-primed mice (⊞).

The present invention meets the needs of the art by providing methods of administering vaccine compositions. These methods permit enhanced mucosal immunity, particularly in the vaginal mucosa, of conventional vaccines by priming the immune system of the mammal prior to delivery of the vaccine. These methods further enhance the immune response to the selected antigen, while suppressing the immune response to the recombinant viral or bacterial delivery vehicle for presentation of the antigen to the immune system.

I. Methods for Enhancing Mucosal Immunity

The invention provides a method of inducing mammalian mucosal immunity to a pathogen that includes the steps of administering via a non-mucosal route of administration an effective amount of a priming DNA vaccine composition and subsequently administering via a mucosal route to the mammal an effective amount of a boosting vaccine composition. This method is based on the discovery that systemic priming of a mammal using a DNA vaccine expressing an antigen a selectively augments or enhances the induction of antigen-specific mucosal immunity upon subsequent immunization or boosting, via a mucosal route, with a composition containing the same antigen. The enhanced mucosal immunity is vastly superior to that induced by other prior art methods of effecting mucosal immunity in a mammal. The method of the invention can be readily adapted to induce or enhance mucosal immunity in a host to any antigen which may be expressed by any of a number of available DNA expression vectors.

By "mucosal immune response" or "mucosal immunity" as the terms are interchangeably used herein, is meant the induction of a humoral (i.e., B cell) and/or cellular (i.e., T cell) response. Most preferably, this immune response is specific for the antigen with which the mammalian host was immunized. Suitably, a humoral mucosal immune response may be assessed by measuring the antigen-specific antibodies present in the mucosal lavage in response to introduction of the desired antigen into the host. In one exemplary embodiment below, the mucosal immune response is assessed by measuring anti-antigen antibody titers and isotype profiles in vaginal lavage of immunized mammals. Most preferably, the antibody response is composed primarily of IgA antibodies. A cellular mucosal immune response may be assessed by measuring the T cell response from lymphocytes isolated from the mucosal area (e.g., vagina or gastrointestinal tract) or from lymph nodes that drain from the mucosal area (for example genital area or gastrointestinal area). However, the invention is not limited to vaginal mucosal immune response; it should be construed to include the immune response at various mucosa of mammals of either gender and of various species.

By "mammalian subject" is meant any male or female mammal. Preferably the mammalian subject is human. However, other primates as well as mammalian species, including without limitation, dogs, cats, cows, horses, pigs, sheep, goats, mice, rabbits, and rats, etc. are also encompassed by this definition.

As used herein, the term "antigen" means an immunogenic peptide or protein which induces an immune response to a pathogen capable of infecting a mammal, including bacteria, viruses, fungi, yeast, parasites and other microorganisms capable of infecting mammalian species. In one aspect, because the method of this invention is directed to the induction of mucosal immunity, selected antigens used in the DNA vaccine and boosting vaccines of this invention are derived from pathogens which invade the mammal via the mucosa. For example, the pathogen may be selected from among the important human sexually-transmitted pathogens for which there is no current effective vaccine. For example, HIV, HPV, HSV-1, HSV-2, *Neisseria gonorrhea*, Chlamydia, and *Treponema pallidum* can provide antigens or DNA sequences encoding antigens for use in the methods of this invention. Thus, antigens suitable for use in the present invention include, but are not limited to, the L1 protein of HPV, the L2 protein of HPV, the E6 protein of HPV, the E7 protein of HPV, the gp41 protein of HIV, the gag protein of HIV, the tet protein of HIV and the gp120 glycoprotein of HIV, among others. Still other pathogens for which such vaccines and vaccine protocols are useful include the pathogens that cause trichomoniasis, candidiasis, hepatitis, scabies, syphilis, and other sexually transmitted diseases. However, the invention is not limited solely to the antigens of sexually-transmitted pathogens. Pathogens which invade via the mucosa also include those that cause respiratory syncytial virus, flu, other upper respiratory conditions, as well as agents which cause intestinal infections. The methods of augmenting mucosal immunity provided herein are readily applicable to vaccine protocols of vaccines to any pathogen against which mucosal immunity is effective. The examples demonstrate the use of HPV L1, E6 and E7 as exemplary antigen, as well as a rabies glycoprotein. Further, the invention encompasses the expression of antigens derived from a wide range of human pathogens to which mucosal immunity is desired. Thus, the invention is not limited by the identity of the particular antigen.

The term "antigen" is further intended to encompass peptide or protein analogs of known or wild-type antigens such as those described above, which analogs may be more soluble or more stable than wild type antigen, and which may also contain mutations or modifications rendering the antigen more immunologically active. Further peptides or proteins which have sequences homologous with a desired antigen's amino acid sequence, where the homologous antigen induces an immune response to the respective pathogen, are also useful. "Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g. five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 50% homologous, more preferably about 70% homologous, even more preferably about 80% homologous and most preferably about 90% homologous to the desired nucleic acid. Genes which are homologous to the desired antigen-encoding sequence should be construed to be included in the invention provided they encode a protein or polypeptide having a biological activity substantially similar to that of the desired antigen. Where in this text, protein and/or DNA sequences are defined by their percent homologies or identities to identified sequences, the algorithms used to calculate the percent homologies or percent identities include the following: the Smith-Waterman algorithm [J. F. Collins et al, 1988, *Comput. Appl. Biosci.*, 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp.417], and the BLAST and FASTA programs [E. G. Shpaer et al, 1996, *Genomics*, 38:179–191 ]. These references are incorporated herein by reference.

Analogs of the antigens described herein can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Modifications (which do not normally alter primary sequence) include in vivo, or in vitro chemical derivatization of polypeptides, e.g., acetylation, or carboxylation. Also included as antigens are proteins modified by glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced as antigens according to this invention are sequences which have phosphorylated amino acid residues, e.g., phosphotyrosine, phosphoserine, or phosphothreonine. Also included as antigens are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The antigens of the invention are not limited to products of any of the specific exemplary processes listed herein. In addition to substantially full length polypeptides, the antigens useful in the present invention include immunologically active fragments of the polypeptides. As used herein, the term "fragment," as applied to a polypeptide, will ordinarily be at least about fifteen contiguous amino acids, typically at least about twenty five contiguous amino acids, more typically at least about forty contiguous amino acids, usually at least about forty five contiguous amino acids and preferably at least about fifty contiguous amino acids in length. A polypeptide or antigen is "immunologically active" if it induces an immune response to the naturally-occurring pathogen.

By the term "vector" as used herein, is meant any self-replicating DNA molecule derived from viral or bacterial species which has been designed to encode an exogenous or heterologous nucleic acid sequence. Thus, the term includes conventional bacterial plasmids. The term also includes non-replicating viruses which transfer a gene from one cell to another. The term should also be construed to include non-plasmid and non-viral compounds which facilitate transfer of nucleic acids into cells, such as, for example, polylysine compounds and the like. Examples of viral vectors include, but are not limited to, adenoviral vectors, poxvirus vectors, retroviral vectors, and the like. Examples of bacterial vectors include, but are not limited to, sequences derived from bacille Calmette Guérin (BCG), Salmonella, Shigella, and Listeria, among others.

A. The Priming Step

The method according to this invention involves "priming" a mammalian subject by administration of a priming DNA vaccine composition. As used in this context, a "priming DNA vaccine composition" defines a composition containing a DNA sequence which encodes an antigen as defined herein. The antigen-encoding sequence is under the control of regulatory sequences directing its expression in a mammalian cell. Thus, as one embodiment the DNA vaccine composition comprises the antigen-encoding DNA sequence operably linked to a suitable promoter which directs its expression, and a suitable physiologically acceptable carrier. Thus, the priming vaccine includes a bacterial plasmid containing the antigen-encoding sequence. Alternatively, the priming vaccine can include simply the DNA sequence encoding the antigen operably linked to regulatory sequences, without further bacterial sequences. Still another embodiment of a suitable DNA priming vaccine is replicating DNA related to the Semliki Forest virus (Sinbus), which also contains the desired antigen-encoding sequence. In the Examples below, exemplary priming DNA vaccines are bacterial plasmids containing an HPV gene as the antigen, e.g., pVRHPV-16E6 and pVRHPV16E7 or a rabies gene as the antigen, e.g., pVRrab.gp or pSG5rab.gp. The priming amount used in the examples is between about 10 $\mu$g and about 50 $\mu$g of plasmid DNA.

By the term "priming" as used herein, is meant any method by which a first immunization using an antigen induces a higher level of immune response to the desired antigen upon subsequent re-immunization with the same antigen when compared with the immune response achieved where the first immunization is either not provided or where the first immunization administered contains a DNA vector which does not express the antigen.

The priming vaccine is preferably administered systemically, i.e., immunization or administration at a site which is not covered by mucosa, that is administration at any site of administration excluding the intranasal, oral, vaginal, intratracheal, intestinal or rectal mucosal surfaces. This systemic administration includes any parenteral routes of administration characterized by physical breaching of a tissue of a subject and administration of the pharmaceutical composition through the breach in the tissue. In particular, parenteral administration is contemplated to include, but is not limited to, intradermal, transdermal, subcutaneous, intraperitoneal, intravenous, intraarterial, intramuscular, or intrasternal injection, intravenous, intraarterial, or kidney dialytic infusion techniques, and so-called "needleless" injections through tissue. Preferably, the systemic, parenteral administration is intramuscular injection. The route of administration of the vaccine may vary depending upon the identity of the pathogen or infection to be prevented or treated.

The priming vaccine may be administered at various sites in the body in a dose dependent manner, which depends on the antigen to which the desired mucosal immune response is being targeted. In the examples described specifically below and in a preferred embodiment, the priming vaccine was administered intramuscularly to mammals. The invention is not limited to the amount or situs of injection(s) or to the pharmaceutical carrier, nor to this immunization protocol. Rather, the priming step encompasses treatment regimens which include a single dose or dosage which is administered hourly, daily, weekly or monthly, or yearly. As an example, the animals treated in the examples received two simultaneous priming injections containing between about 10 $\mu$g to about 50 $\mu$g of plasmid in 50 $\mu$l of water or saline, administered intramuscularly, one in each quadricep muscle. The amount or site of injection is desirably selected based upon the identity and condition of the mammal being vaccinated.

By "priming amount" as that term is used herein, is meant the amount of DNA vaccine expressing the target antigen which induces a measurable mucosal immune response upon subsequent intranasal immunization with a boosting vaccine composition comprising the same antigen when compared with the mucosal immune response generated by priming immunization with an empty DNA vector, ie., a vector which does not contain the target antigen gene, or where no priming immunization is administered at all. A desirable priming amount or dosage of the priming DNA vaccine composition ranges between about 1 $\mu$g to about 10,000 $\mu$g of the DNA vaccine. Dosages may vary from about 1 $\mu$g to 1000 $\mu$g DNA vaccine/kg of subject body weight.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of a genetic adjuvant. The term "genetic adjuvant" defines any biologically active factor, such as cytokine, an interleukin, a chemokine, a ligands, and optimally combinations thereof, which is expressed by a plasmid-based vector, and which, when administered with the priming DNA vaccine encoding an antigen, enhances the antigen-specific mucosal immune response compared with the immune response generated upon priming with the DNA vaccine encoding the antigen only. In one embodiment, the genetic adjuvant is Interleukin-5. In the examples below, interleukin-5 expressed by a plasmid vector (pcDNA3IL-5) was used herein as a genetic adjuvant which was co-administered with the DNA vaccine expressing the rabies virus glycoprotein antigen to obtain an enhanced antibody response. However, in another suitable embodiment, the genetic adjuvant is Interleukin4. This genetic adjuvant is particularly desirable where an enhanced cellular immune response is desired. Other desirable genetic adjuvants include, without limitation, the DNA sequences encoding IL-10, IL-12, IL-13, the interferons (IFNs) (for example, IFN-$\alpha$, IFN-$\beta$, and IFN-$\gamma$), and preferred combinations thereof Still other such biologically active factors that enhance the antigen-specific immune response may be readily selected by one of skill in the art, and a suitable plasmid vector containing the same factors constructed by known techniques.

B. The Boosting Step

Preferably, a boosting vaccine composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine.

As used herein the term "boosting vaccine composition" includes, as one embodiment, a composition containing the same antigen as encoded in the priming DNA vaccine, but in the form of a protein or peptide, which composition induces a mucosal immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the composition is in a form which can be absorbed by the mucosa, and most specifically, by the nasal mucosa, and that the antigen of the vaccine composition is the same antigen as that encoded by the DNA vaccine.

For example, one embodiment of a boosting vaccine composition that can be administered intranasally is a replication competent or replication defective recombinant virus containing the DNA sequence encoding the antigen. Adenoviruses, which naturally invade their host through the airways, infect cells of the airways readily upon intranasal application and induce a strong immune response without the need for adjuvants such as cholera toxin (CT) or relatives thereof commonly used to enhance mucosal immunity upon vaccination with proteins or nucleic acids. Such adjuvants, although generally tolerated by experimental animals, cause adverse effects in human subjects including prohibitive diarrheal purges.

A particularly preferred recombinant virus is a replication defective recombinant adenovirus. E1-deleted adenoviral recombinants have a number of distinctive advantages as booster vaccine compositions for inducing mucosal immunity to a target gene inserted into the adenovirus according to this invention. They are replication-defective and thus they are safe, as was demonstrated in pre-clinical gene therapy trials where non-human primates were treated with high doses of the recombinants which were well above the doses needed for vaccination without adverse effects [Simon et al., 1993, Hum. Gene Therapy, 4:771–780)]. Deletion of the E1 gene renders this vector non-cytopathic thereby lengthening the duration of antigen expression by this adenovirus recombinant in infected cells. E1-deleted adenoviral recombinants induce strong B cell responses both systemically and at mucosal sites which provide an initial barrier to infection. They also, due to a defect in expression of the E3 gene which is known to down-regulate MHC class I expression, stimulate a potent cytolytic T cell response which is required as a second defense mechanism against intracellular pathogens which evaded neutralization by antibodies at the mucosal barrier. In one embodiment, exemplified below, the boosting vaccine composition is an E1-deleted adenoviral recombinant virus of human strain 5 which expresses the selected antigen for induction of a vaginal antibody response upon intranasal immunization. However, in another embodiment, another virus that can be employed as the carrier portion of the boosting composition is, e.g., a recombinant vaccinia, retrovirus, or an avian poxvirus.

Another example of a boosting composition is a bacterial recombinant vector containing the DNA sequence encoding the antigen in operable association with regulatory sequences directing expression of the antigen in tissues of the mammal. One example is a recombinant BCG vector. Other examples include recombinant bacterial vectors based on Salmonella, Shigella, and Listeria, among others. Still another example of a boosting composition is a naked DNA sequence encoding the antigen in operable association with regulatory sequences directing expression of the antigen in tissues of the mammal but containing no additional vector sequences. These vaccines may further contain pharmaceutically suitable or physiologically acceptable carriers.

In still additional embodiments, the boosting vaccines can include a variety of boosting antigen compositions which comprise an antigen including, but not limited to, vaccines containing one or more pathogenic proteins or peptides in protein form (intact or denatured), heat-killed recombinant vaccines, inactivated whole microorganisms, and the like, all with or without adjuvants.

A preferred booster composition is a recombinant virus or bacterium expressing the target antigen, administered intranasally. However, the invention should not be construed as being limited to boosting with a recombinant virus or bacteria, as described above.

The boosting composition is administered via a selected mucosa. The presently preferred route of boosting composition administration is the intranasal route. Delivery can be accomplished by aerosol, nebulizer, or by depositing a liquid in the nasal cavity. Alternatively, boosting may be by suppository, enema, or vaginal douche or other inhalation methods where direct immunization at a different mucosal surface of interest is desired. As illustrated in the examples below, when the booster is administered intranasally, the priming boosting protocol of this invention induces in a mammal an enhanced or augmented mucosal immune response, and particularly enhanced vaginal antibody secretion, to the antigen presented by the DNA vaccine and booster composition. However, boosting may also be accomplished via the vaginal, rectal, oral or tracheal mucosa.

By "effective amount of the boosting vaccine" as that term is used herein, is meant the amount of antigen which induces a mucosal immune response upon mucosal immunization in a mammal which has previously received a priming amount of the same antigen systemically between about one week to about 6 months prior to boosting. An effective amount of the boosting composition depends upon the form of the boosting vaccine, e.g., antigenic protein or recombinant virus or bacterial vectors encoding the antigen. For example, where the boosting composition is a recombinant virus, the effective amount may range from about $10^4$ particle forming unit (pfu) to $10^8$ pfu of adenovirus recombinant per kg mammalian body weight. This amount may be adjusted as desired for larger mammals, e.g., between about $10^8$ to $10^{15}$ pfu for humans. Alternatively, for other viruses the dosage may be from $10^6$ to about $10^{16}$ viral particles per dose. In an exemplary embodiment of the examples below, the boosting composition is AdHPV-16L1 adenovirus recombinant and the effective amount is $2 \times 10^6$ pfu of per mouse (e.g., about 25 g body weight). Where the boosting vaccine is a bacterial vector, the dosage may be between about 1 to about 1000 $\mu$g DNA per kg body weight of subject. This amount may be similarly adjusted upwards as desired for larger mammals. The amount of the boosting vaccine in protein form, e.g., protein vaccine, inactivated microorganism, etc. may be selected from dosages typical in the art for such vaccines. Selection of the effective amount of the boosting composition is within the skill of the art, given the teachings of this invention.

The method of this invention is demonstrated in the examples below in which the selected antigen present in the priming DNA vaccine and in the boosting composition is an HPV L1, E6 or E7 protein. According to this invention, the induction of antigen-specific vaginal antibody secretion upon intranasal boosting immunization with an adenoviral recombinant expressing the antigen can be significantly augmented by priming via systemic immunization with a DNA vaccine expressing the same antigen. The present invention demonstrates that such a combination vaccine regimen may provide a suitable method for preventative treatment of sexually transmitted infectious agents for which there is currently no effective vaccine method.

As illustrated in the Examples 1–9 below, the present invention discloses the achievement of genital secretion of antigen-specific antibodies of the IgA and IgG2a isotypes up to at least 6 months (the latest time point tested) after i.n. immunization with an adenoviral recombinant as the boosting composition. Further, the mucosal immune response was markedly enhanced and was prolonged by a second dose of the homologous construct also given intranasally. The first immunization of a DNA vaccine had not resulted in sterilizing immunity.

The examples below demonstrated that, surprisingly, a DNA vaccine, when administered intratracheally in a saline solution, induced a low serum antibody response but failed to cause measurable secretion of specific antibodies at the vaginal mucosa. However, the same DNA vaccine administered intramuscularly resulted in high serum antibody titers and low titers of IgG2a antibodies in vaginal secretion. Either route of priming promoted a vaginal antibody response to an intranasal booster immunization with the adenovirus recombinant. DNA priming strongly favored the development of serum IgG2a antibodies, indicative of a Th1 response, upon booster immunization. DNA priming also augmented the vaginal antibody response including secretion of IgA which is considered an antibody isotype promoted by IL-4 secreting Th2 cells [Xu-Amano et al., 1993, *J. Exp. Med.* 178:1309–1320] and by mucosal T cells expressing the γ/δ receptor [Fujihashi, 1996, *J. Ep. Med.* 183:1929–1935].

Additionally, the enhanced mucosal immune response to a target antigen observed by first priming with a DNA vaccine expressing the antigen was increased even further by co-administration of a genetic adjuvant (e.g., pcDNA3IL-5) expressing a cytokine along with the DNA vaccine. Thus, systemic co-priming with a genetic adjuvant further enhanced the remarkable increase in mucosal immune response observed with systemic DNA vaccine priming upon subsequent intranasal boosting with a recombinant vaccine expressing the desired antigen.

As specifically disclosed below, the present invention demonstrates that DNA vaccines expressing an antigen given systemically, with or without a genetic adjuvant, can effectively prime a vaginal antibody response including secretion of specific IgA upon intranasal boosting immunization with a replication-defective adenoviral recombinant expressing the same antigen. The invention disclosed herein therefore presents a novel, safe and effective vaccine regimen which does not require the use of toxic adjuvants and which is particularly suitable for prophylactic treatment of important human sexually transmitted diseases for which there are presently no effective vaccines.

II. Methods of Reducing Unwanted Immune Response to Vaccine Carrier

Also an embodiment of the present invention is a related method of reducing the immune response to the vaccine carrier or vehicle of the boosting vaccine, particularly where the carrier is a recombinant virus or recombinant bacterium. This method involves administering to a mammalian subject an effective amount of a priming DNA vaccine composition prior to administering a recombinant vaccine composition which comprises a recombinant carrier containing a DNA sequence encoding the antigen under the control of regulatory sequences directing expression of the antigen in a mammalian cell. In this embodiment of a method of this invention, the priming DNA vaccine may be described as defined above with one significant limitation. The priming DNA vaccine must encode no antigenic carrier proteins or peptides (e.g., viral proteins or bacterial proteins or antigens). More specifically, outside of the DNA sequence that encodes the selected antigen under the control of regulatory sequences directing expression thereof in a mammalian cell or tissue, the DNA vaccine must present to the subject no antigens which would evoke an anti-carrier immune response. Both the DNA encoding the antigen itself, and the regulatory sequences may contain viral or bacterial components, e.g., a viral or bacterial promoter or regulatory sequence. For example, the antigen may be a bacterial or viral antigen. However, the remainder of the DNA vaccine encodes no carrier protein, and preferably the carrier proteins which are part of the DNA vaccine are not derived from the recombinant carrier which is subsequently administered as a recombinant vaccine. Upon administration of the recombinant vaccine, the immune response to the desired antigen is enhanced and the immune response to the recombinant carrier is reduced.

Unlike the first method of this invention, this method does not rely upon route of administration. Thus, the DNA vaccine composition and the recombinant boosting vaccine may be administered using any suitable route of administration conventional used for administering vaccines to mammalian patients. However, the examples below demonstrate that the systemic administration of the DNA vaccine followed by intranasal administration of the recombinant boosting vaccine does produce this result. It is anticipated that the same result should be caused by other routes of administration. The dosages of the DNA vaccine and the recombinant boosting vaccines are conventional, and may be analogous to the dosage amounts described above for the DNA vaccine and boosting composition (where the boosting composition is a recombinant virus or bacterium), as described above.

As one embodiment, the DNA vaccine was a bacterial plasmid encoding an HPV L1, E6 or E7 protein and the recombinant boosting vaccine was the recombinant adenovirus human type 5 containing the same antigen. It is known that pre-existing neutralizing antibodies in humans to human adenovirus type 5 may impair the immune response to the antigen expressed by using adenovirus as the recombinant vaccine carrier. In order to circumvent this potential problem and to optimize the effect of "prime-boost" vaccine regimens, the ability of DNA vaccines to prime the genital mucosa immune response to i.n. immunization with the adenoviral recombinant was examined in the examples below. The DNA vaccine when administered intramuscularly as a priming vehicle, significantly enhanced the vaginal IgA and IgG2a secretion induced upon subsequent boosting intranasally by an adenovirus recombinant expressing the same target antigen. This immunization regimen strongly inhibits the development of an antibody response to the adenoviral antigens of the vaccine carrier, thereby circumventing the main drawback of using adenovirus vectors to induce a mucosal immune response.

Thus, it was unexpectedly found that the DNA vaccine had a profound effect on the immune response to the adenoviral antigens of the vaccine carrier. Priming with the DNA vaccine not only augmented the antibody response to the selected antigen, but also strongly inhibited the central and mucosal B cell response to the adenoviral vaccine carrier. The nearly complete suppression of the B cell response to the vaccine carrier is expected to allow its subsequent use for additional booster immunization or for induction of primary immune responses to additional antigens. Additionally, the same response is anticipated where the vaccine carrier is bacterial in origin.

III. Methods of Making Constricts Useful in the Methods of This Invention

The DNA vaccine compositions and boosting vaccine compositions useful in this invention may be prepared by conventional methods known to one of skill in the art. The methods for construction of the DNA vaccines of the invention or the plasmid or recombinant vectors of the boosting composition are described in conventional texts, such as Burger et al., *J. Gen. Virol.*, 12:359–367 (1991), and are well-known in the art. See also Sambrook et al., 1989, *Molecular Cloning: A Laboratory Manual*, Cold Spring Harbor Laboratory Press, New York; and Ausubel et al., 1997, *Current Protocols in Molecular Biology*, Green & Wiley, New York. For example, DNA or RNA sequences which encode the selected antigens or sequences sufficiently homologous to known antigens to induce immune responses may be obtained by following well known procedures described in the art for the isolation of DNA or RNA molecules from a variety of microorganism sources. Alternatively, DNA sequences encoding the antigen may be synthesized in a nucleic acid synthesizer. Thus, the invention should be construed to include synthetic forms of nucleic acids encoding the antigen. Other DNA or recombinant bacterial plasmids or viral vectors which contain such isolated nucleic acid encoding a target antigen and which are preferably capable of directing expression of the target antigen protein encoded by the nucleic acid in a host cell; and cells containing such vectors, either eukaryotic or prokaryotic cells, preferably eukaryotic cells are also prepared by known techniques.

To ensure expression of the antigen by the DNA vaccine or boosting composition in plasmid or viral vector form, the antigen-encoding nucleic acid sequences are operably linked to a promoter/regulatory region capable of driving high levels of expression of the antigen in cells. Many such promoter/regulatory sequences are available in the art including, but not limited to, for example, the human cytomegalovirus immediate early promoter/enhancer sequence, the SV40 early promoter, the Rous sarcoma virus promoter and other mammalian promoter/enhancer sequences. By the term "promoter/regulatory sequence" is meant a DNA sequence which is required for expression of a nucleic acid operably linked to the promoter/regulatory sequence. In some instances, the promoter/regulatory sequence may function in a tissue specific manner, in that, the promoter/regulatory sequence is only capable of driving expression in a cell of a particular tissue type. In some instances, this sequence may be the core promoter sequence and in other instances, this sequence may also include an enhancer sequence and other regulatory elements which are required for expression in a tissue-specific manner.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other. Preferably, when the nucleic acid encoding antigen further comprises a promoter/regulatory sequence, the promoter/regulatory is positioned at the 5' end of the target antigen coding sequence such that it drives expression of the antigen in a cell.

Unless otherwise indicated, selection of any particular plasmid vector or other DNA vector or viral vector is not a limiting factor in this invention and other DNA or viral vectors may be substituted for those disclosed herein upon a reading of the present disclosure. It is well within the skill of the artisan to choose particular promoter/regulatory sequences and operably link those promoter/regulatory sequences to a DNA sequence encoding a desired antigen. Such technology is well known in the art and is described, for example, in Sambrook, supra, and Ausubel, supra.

Further, where the boosting composition is in the form of protein, it is within the skill of the art to isolate and produce protein compositions for vaccine use.

The selected DNA vaccine and boosting compositions are desirably formulated into pharmaceutical compositions suitable for administering the priming DNA vaccine or the boosting vaccine. Such formulations comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

IV. A Kit of the Invention

Also included in the invention is a kit for inducing and augmenting a mucosal immune response to a target antigen. Such a kit preferably comprises a priming amount of a DNA vaccine composition useful for priming the immune response to a target antigen or an immunologically active fragment thereof. Also included is an effective amount of a boosting vaccine composition comprising the same antigen or a sequence encoding the same antigen. The kit may also include a genetic adjuvant DNA composition encoding a factor such as a cytokine which is administered with the priming DNA vaccine encoding the antigen.

Other components of the kit include applicators for administering each composition. By the term "applicator" as the term is used herein, is meant any device including but not limited to a hypodermic syringe, gene gun, nebulizer, dropper, bronchoscope, suppository, impregnated or coated vaginally-insertable material such as a tampon, douche preparation, solution for vaginal irrigation, retention enema preparation, suppository, or solution for rectal or colonic irrigation for applying the priming DNA vaccine and/or the boosting antigen either systemically or mucosally, respectively, to the human or veterinary patient.

Still another component involves instructions for using the kit. The instructions for using the kit depend on the antigen for which the kit is to be used. The kit may also include instructions on how to apply the priming DNA vaccine or the boosting vaccine composition, e.g., a recombinant virus, using the applicator provided therewith. As one example, in the case of mucosal immunity employing the compositions of the examples below, the instructions comprise directions on how to administer the priming DNA vaccine composition intramuscularly and how to subsequently administer the boosting composition, e.g., the adenovirus recombinant, intranasally. These instructions simply embody the examples provided herein.

The invention is further described in detail by reference to the following experimental examples. These examples are provided for purposes of illustration only, and are not intended to be limiting unless otherwise specified. The invention should not be construed as being limited to the use of the specific selected antigens disclosed herein in the examples, and should further not be construed as being limited to the use of the particular DNA plasmid vectors employed as the priming DNA vaccines, nor to the particular recombinant adenovirus vaccine described below as the boosting composition. Thus, the invention encompasses any and all variations which become evident as a result of the teaching provided herein.

EXAMPLE 1: INTRANASAL IMMUNIZATION WITH AN ADENOVIRAL RECOMBINANT INDUCES ANTIBODY SECRETION AT THE GENITAL MUCOSA

A. The Recombinant Adenovirus

The replication defective, E-1 deleted, adenovirus (human strain 5) recombinant Adrab.gp is described in U.S. Pat. No. 5,698,202; also International Patent Publication No. WO 96/39178, published Dec. 12, 1996, and available from the American Type Culture Collection under Accession No. VR-2554. It contains the full-length rabies virus glycoprotein of the Evelyn Rokitniki Abelseth (ERA) strain as the selected antigen under control of the cytomegalovirus (CMV) promoter in the site of the E1 deletion of a human type 5 adenovirus having a partial E3 deletion. Adrab.gp was grown on E1-transfected 293 cells grown in Dulbecco's Modified Eagles medium (DMEM) supplemented with 10% fetal bovine serum (FBS) and antibiotics [Xiang et al., *Virol.*, 219:220–227 (1996)].

B. Protocol

Groups of 4–5 female 6–10 week old C3H/He mice [Jackson Laboratory, Bar Harbor, Minn.) were immunized intranasally or subcutaneously with Adrab.gp. The Adrab.gp, was administered intranasally by depositing 50 $\mu$l liquid containing $2 \times 10^6$ pfu on both nostrils. Alternatively, the Adrab.gp was administered subcutaneously at $2 \times 10^6$ pfu in 200 $\mu$l of saline. Naive, non-immunized mice formed the control group. Sera and vaginal lavage were harvested from the mice at 2 weeks and 6 weeks after vaccination.

C. Preparation of Samples

Mouse serum was prepared from blood obtained by retro-orbital puncture. Sera were tested at serial dilutions starting with a 1:200 dilution for all titrations. For isotype determination, sera were tested at a 1:800 dilution.

Vaginal lavage was obtained by rinsing the vaginal cavity 3 times with 50 $\mu$l of sterile saline. Debris was removed by centrifugation. In most experiments, vaginal lavage fluid was tested immediately after harvesting at a starting dilution of 1:2 of the wash solution for the titration experiments. A 1:8 dilution of the lavage fluid was used for isotype mapping. In some of the experiments, total immunoglobulin (Ig) was determined in several different pooled lavage fluids by ELISA using microtiter plates coated with a rabbit anti-mouse Ig to assess any potential variability in the ratio of harvested lavage fluid to washing fluid. The variability of total Ig amount in vaginal lavage fluids of different groups of mice was negligible.

D. Enzyme Linked Immunoadsorbant Assay

Sera and vaginal lavage were tested for antibodies to rabies virus on microtiter plate wells coated with purified rabies virus of the ERA strain, which was propagated and titrated on baby hamster kidney BHK)-21 cells and was inactivated by betapropionolactone treatment (ERA-BPL) [Wiktor, 1973, In: *Laboratory Techniques in Rabies,* 2nd ed., vol. 23, p. 101–120, Kaplan and Koprowski, eds., World Health Organization Monograph, Geneva; and Wiktor et al., *J. Virol.,* 21:626–633 (1977)].

Sera and vaginal lavage were tested for antibodies to rabies virus on microtiter plate wells coated with purified wild-type adenovirus virus [Xiang et al., *Virol,* 199:132–140 (1994);Vector Core Facility of the Institute of Human Gene Therapy, University of Pennsylvania (Philadelphia, Pa.)]. The isotypes of antibodies were determined using an isotyping kit and a 1:200 dilution of sera [Wang et al., *Virol.,* 228:278–284 (1997)]. All assays were conducted using duplicate or triplicate samples for each dilution. Standard deviations were generally below 5% of the mean.

E. Results of Assays

The mice developed high serum antibodies to rabies virus of a mixed isotype profile predominated by IgG2a (see FIGS. 1A through 1H). While the magnitude and the isotype profile of the B cell responses to rabies virus were comparable using either route of immunization, higher levels of induction of antirabies virus antibody secretion at the vaginal mucosa were present following intranasal immunization, although measurable titers of IgG2a were also induced in vaginal lavage by subcutaneous vaccination.

Soon after vaccination (i.e., after 2 weeks), intranasal inoculation resulted in high levels of specific IgA and IgG2a, as well as low amounts of IgG1 and IgG2b in vaginal secretions. The IgA response that initially prevailed was transient and declined markedly by the sixth week after immunization while the IgG2a titers to rabies virus remained stable.

The vaginal antibody response to the E1-deleted replication-defective adenoviral recombinant expressing the rabies virus glycoprotein as the test antigen was initially examined using a number of routes of immunization including intranasal, oral, vaginal and rectal. While all of these routes, with the exception of oral immunization, resulted in seroconversion and in some local mucosal antibody secretion, the intranasal route was by far the most efficacious in inducing a mucosal immune response to the antigen, particularly vaginal secretion of IgA and IgG (mainly IgG2a).

These data demonstrate, inter alia, that intranasal priming followed by intranasal boosting with a recombinant viral vector induced a mucosal immune response at a distal site, ie., the vaginal mucosa. That is, mice immunized intranasally with an E1-deleted replication-defective adenoviral recombinant expressing the rabies virus glycoprotein as the test antigen developed a vaginal antibody response composed initially mainly of IgA which at later time points was replaced by IgG2a. The present invention discloses that vaginal antibody titers, including IgA titers, are augmented and sustained by a second dose of the same adenoviral recombinant also given intranasally.

EXAMPLE 2: A PRIMING INTRANASAL IMMUNIZATION WITH AN ADENOVIRAL RECOMBINANT FOLLOWED BY A BOOSTING DOSE INDUCES AUGMENTED ANTIBODY SECRETION AT THE GENITAL MUCOSA

A. Protocol

Groups of 4–5 female 6–10 week old C3H/He mice were immunized intranasally with the Adrab.gp described in Example 1 administered by depositing 50 μl liquid containing 2×10⁶ pfu on both nostrils. Two months later, the mice were boosted with the same dose of the Adrab.gp virus given either intranasally or boosted subcutaneously with Adrab.gp at 2×10⁶ pfu in 200 μl of saline. A control group was primed but not boosted. Sera and vaginal lavage were harvested from the mice at 1 month and 4 months after boosting, and samples were prepared and assayed as described in Example 1.

B. Results

As shown in FIGS. 2A through 2I, both routes of booster immunization enhanced antibody titers to the transgene product measured 1 and 4 months later in both sera and vaginal lavage. While the subcutaneous booster immunization gave the highest increase of serum antibody titers, intranasal immunization given twice resulted in the most pronounced antibody titers in vaginal secretions. Antibody isotypes in vaginal lavage tested 4 months after immunization exhibited a predominance of IgG2a antibodies for all of the groups although substantial levels of IgA were detectable in the vaginal lavage of mice that had received the vaccine twice by the intranasal route.

The data of Example 2 below demonstrates that the adenoviral recombinant, when administered intranasally, induced a mucosal antibody response in the genital tract which was augmented and sustained by a second intranasal dose of the same vaccine. Without wishing to be bound by theory, it seems that expression of the transgene product depends on the synthesis of viral antigens in infected cells; hence, reduction of the infection rate by an immune response may negatively affect the load of the transgene product and, thus, may diminish the magnitude of the secondary immune response.

EXAMPLE 3: INTRAMUSCULAR PRIMING WITH A DNA VACCINE STRONGLY AUGMENTS THE MUCOSAL ANTIBODY RESPONSE UPON INTRANASAL BOOSTING WITH THE ADRAB.GP RECOMBINANT VIRUS

In this example, the vaccine method of the invention is demonstrated in which a priming dose of a DNA vaccine, expressing the same antigen of the rabies virus was used for priming a vaginal immune response to a boosting dose given intranasally of the adenoviral recombinant Adrab.gp of Example 1.

A. The DNA Vaccine

Two different priming DNA vaccine compositions were designed utilizing recombinant DNA techniques performed using standard methods as described by Sambrook et al., *Molecular Cloning: A Laboratory Manual,* Cold Spring Harbor Laboratory Press, New York 91989) and by Ausubel et al., *Current Protocols in Molecular Biology,* Green & Wiley, New York (1997).

One exemplary DNA vaccine employs the pSG5rab.gp vector, which is a bacterial plasmid expressing as the selected antigen against which an immune response was desired, the glycoprotein (gp) of the ERA strain of rabies virus [U.S. Pat. No. 4,393,201]. This plasmid vector contains cDNA encoding the target antigen, i.e., the rabies gp gene, operably linked to and under the control of the SV40 early promoter [Burger el al., *J. Gen. Virol.,*72:359–367 (1991); Xiang el al., *Virol.,* 199:132–140 (1994)]. This plasmid vector, when it is deleted of the cDNA encoding the target antigen is referred to as "pSG5".

Another DNA vaccine is the pVRrab.gp vector, which expresses the same rabies antigen under the control of the CMV promoter in the plasmid vector pVR1012.2 vector [Vical, Inc., San Diego, Calif.]. pVRrab.gp was constructed by cloning the rabies virus glycoprotein gene into the multicloning site downstream of the CMV promoter in this vector. The kanamycin resistance gene of the original vector was replaced with the ampicillin resistance gene. The resulting vector described in International Publication No. WO96/39178 was subsequently analyzed by restriction enzyme digest and, upon transient transfection of BHK-21 cells, grown in Dulbecco's Modified Eagles medium (DMEM) supplemented with 10% fetal bovine serum (FBS) and antibiotics, for appropriate expression of the viral glycoprotein using a specific monoclonal antibody in an indirect immunofluorescence assay followed by analysis in a fluorescent activated cell sorter [Xiang et al., *Virol.,* 99:132–140(1994)].

The vectors were expanded in transformed *E. coli* strain DH5α cells grown in Luria-Bertani (LB) medium supplemented with ampicillin, and were purified using the Qiagen Mega Purification kit according to the manufacturer's specification. DNA was quantitated by electrophoresis on an agarose gel against a known standard.

B. Protocol

Groups of 4–5 female 6–10 week old C3H/He mice were injected with 10–50 $\mu g$ of one of the DNA vaccine compositions described in part A above. The DNA vaccine compositions were administered in 50 $\mu l$ of either saline or water into both quadricep muscles, dividing the dose equally to reduce variability. One group of mice were primed with the DNA vaccine given directly intratracheally. Control mice were primed with a control plasmid without a gene insert. The boosting composition, Adrab.gp, was administered between 6 and 12 weeks later intranasally at $2\times10^6$ pfu per mouse by depositing 50 $\mu l$ liquid containing $2\times10^6$ pfu on both nostrils. Sera and vaginal lavage were harvested from the mice just prior to the booster immunization and then at various times after boosting (10 days, one month, two months, and four months), and samples were prepared and assayed as described in Example 1.

In a modification of this protocol, the mice were also primed with 50 $\mu g$ of the pSG5rab.gp vaccine and boosted with the Adrab.gp given intranasally 6 weeks later.

C. Results

The results of the experimental protocol were consistent regardless of the dose of the plasmid vector (10 or 50 $\mu g$), the type of the vector construct (pSG5rab.gp or pVRrab.gp), or the route of priming (intranasally versus intratracheally).

The data depicted in FIGS. 3A through 3R are the results of a representative experiment with the pVRrab.gp vector given at 40 $\mu g$ intramuscularly. Prior to boosting, the mice had readily detectable serum antibody titers while titers in vaginal lavage were barely detectable. Booster immunization intranasally with the Adrab.gp booster augmented serum and vaginal lavage antibody titers which were tested 10 days later. After 1 month, the serum antibody titer of mice primed with either the DNA vaccine or the empty control construct prior to intranasal vaccination with the Adrab.gp recombinant became comparable in magnitude. However, vaginal lavage antibody titers to rabies virus were clearly superior in DNA vaccine-primed mice compared with control mice. This difference was sustained for 4 months.

In addition to IgA which was initially the predominant isotype, DNA-vaccine-primed mice also generated IgG2a antibodies to rabies virus in their vaginal secretion which were present at higher levels compared with antibodies of the IgA isotype 4 months after booster immunization. DNA vaccine-primed mice developed a highly skewed Th1 type serum antibody response that was almost exclusively composed of IgG2a while control mice had, in addition, substantial levels of IgG1 and IgG2b antibodies to rabies virus.

The data in FIGS. 4A through 4D illustrates the results in the modified experiment with pSG5rab.gp as the priming DNA vaccine. Prior to the booster immunization, DNA-vaccinated mice still had serum antibodies and low but detectable vaginal lavage antibodies to rabies virus. Sera and vaginal lavage were tested 6 weeks later for antibodies to rabies virus and for antibodies to adenovirus. pSG5rab.gp-primed mice developed slightly enhanced serum antibody titers upon booster immunization and clearly superior titers in vaginal lavage when compared to control mice confirming results obtained with the pVRrab.gp vector. The magnitude of titers to the adenoviral antigens was reversed, i.e., mice primed with the DNA vaccine to rabies virus only developed marginal serum and vaginal lavage titers to adenoviral antigens while unprimed Adrab.gp immunized mice developed substantial antibody titers at both sites to adenovirus antigens, indicating that the pre-existing immune response to the plasmid encoded antigen had actively inhibited the immune response to the vaccine carrier.

EXAMPLE 4. PRIMING WITH A GENETIC ADJUVANT EXPRESSING INTERLEUKIN-5 CO-ADMINISTERED WITH THE DNA VACCINE FURTHER ENHANCES THE MUCOSAL IMMUNE RESPONSE TO ADMINISTRATION OF THE BOOSTING VACCINE

Upon the remarkable observation that systemic priming augmented the mucosal immune response upon intranasal boosting of the experiments of Example 3, this example further modifies the priming and boosting method of this invention by further augmenting the mucosal immune response by co-priming with a genetic adjuvant.

A. An Exemplary Genetic Adjuvant

An exemplary genetic adjuvant used in this example is the bacterial vector pcDNA3IL-5, which contains the sequence encoding human interleukin 5 under the control of WHAT promoter. This plasmid vector was designed by conventional methods as disclosed above in Example 2.

B. Protocol

Five groups of 4–5 female 6–10 week old C3H/He mice were treated as follows: One group of mice were primed with 10–50 μg of the DNA vaccine of pSG5rab.gp administered in 50 μl of either saline or water into both quadricep muscles, dividing the dose equally to reduce variability as described in Example 3. A second group of mice were primed with the same dose and using the same route of pSG5 empty vector only (i.e., pSG5rab.gp without the rabies gp gene). A third group of mice were given a combination of pSG5rab.gp (50 μg) with the genetic adjuvant pcDNA3IL-5 encoding interleukin-5 (50 μg). A fourth group of mice were primed with pcDNA3IL-5 only. Finally, the fifth control group mice were not immunized at all.

The boosting composition, Adrab.gp, was administered to all five groups between 6 and 12 weeks later intranasally at $2 \times 10^6$ pfu per mouse by depositing 50 μl liquid containing $2 \times 10^6$ pfu on both nostrils. Sera and vaginal lavage were harvested from the mice and samples were prepared and assayed for antibody titers and isotypes at 4 and at 10 weeks after priming with the DNA vaccine(s) and again at 5 days and 10 days after boosting, as described in Example 1.

C. Results

Figure 5A:
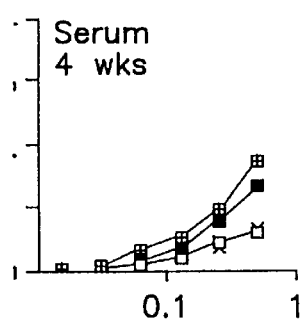
FIG. 5A is a graph depicting the antibody titers in the sera of mice primed with a DNA vaccine to rabies virus (pSG5rab.gp) administered together with a plasmid vector encoding interleukin (IL)-5 (pcDNA3IL-5). Sera were assayed at 4 weeks after priming with pSG5rab.gp/pcDNA3IL-5. The serum antirabies virus antibody titers of mice primed with pSG5rab.gp only (⊞), pSG5rab.gp/pcDNA3IL5 (■), pcDNA3IL-5 only (□), pSG5 empty vector (X), and naive normal mice (+) were measured at 4 weeks after priming.
Figure 5B:
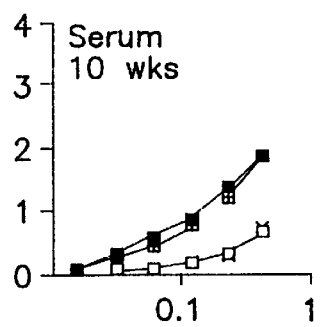
FIG. 5B is a graph depicting the antibody titers in the sera of mice of FIG. 5A assayed at 10 weeks after priming with pSG5rab.gp/pcDNA3IL-5. The symbols are as in FIG. 5A.
Figure 5C:
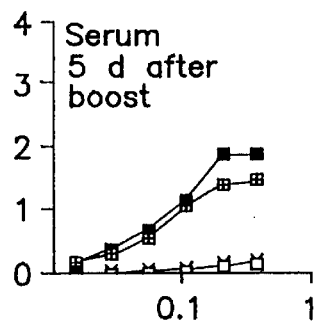
FIG. 5C is a graph depicting the antibody titers in the sera of the mice of FIGS. 5A and 5B, measured 5 days after the mice were boosted i.n. with 2×10⁵ pfu of Adrab.gp recombinant. The symbols are as in FIG. 5A.
Figure 5D:
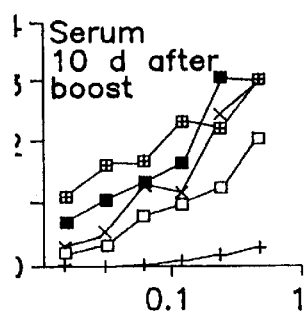
FIG. 5D is a graph depicting the antibody titers in the sera of the mice of FIGS. 5A and 5B, measured 10 days after the mice were boosted i.n. with 2×10⁵ pfu of Adrab.gp recombinant. The symbols are as in FIG. 5A.
Figure 5E:
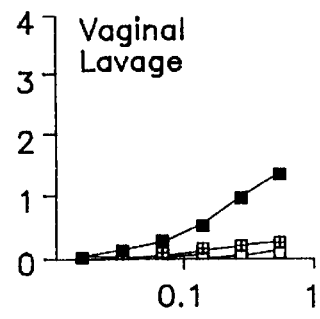
FIG. 5E is a graph depicting the antibody titers in the vaginal lavage of the mice of FIG. 5A assayed at 4 weeks after priming. The symbols are as in FIG. 5A.
Figure 5F:
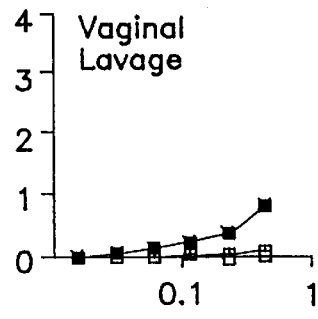
FIG. 5F is a graph depicting the antibody titers in the vaginal lavage of mice of FIG. 5A assayed at 10 weeks after priming with pSG5rab.gp/pcDNA3IL-5. The symbols are as in FIG. 5A.
Figure 5G:
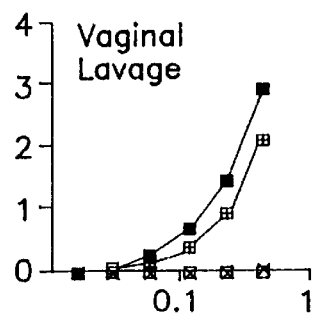
FIG. 5G is a graph depicting the antibody titers in the vaginal lavage of the mice of FIGS. 5E and 5F, measured 5 days after the mice were boosted i.n. with 2×10⁵ pfu of Adrab.gp recombinant. The symbols are as in FIG. 5A.
Figure 5H:
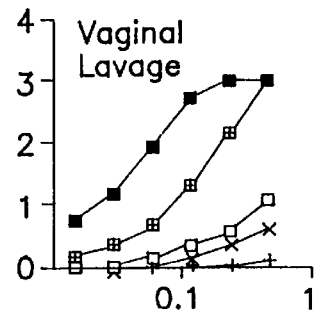
FIG. 5H is a graph depicting the antibody titers in the vaginal lavage of the mice of FIGS. 5E and 5F, measured 10 days after the mice were boosted i.n. with 2×10⁵ pfu of Adrab.gp recombinant. The symbols are as in FIG. 5A.
Figure 5I:
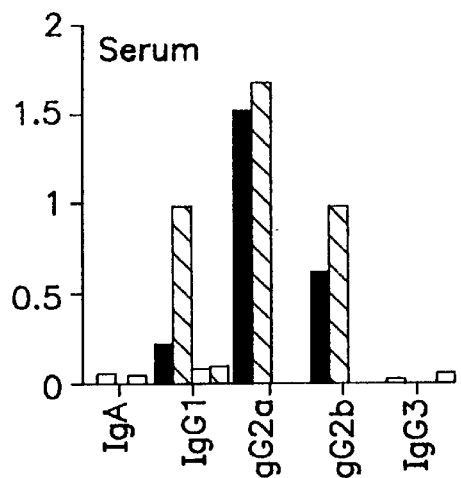
FIG. 5I is a bar graph depicting the isotypes of antirabies virus antibodies in the sera of mice described in FIG. 5A assayed at 4 weeks after priming. The symbols are for mice administered pSG5rab.gp only (striped bar), pSG5rab.gp/pcDNA3IL-5 (■); pcDNA3IL-5 only (dotted bar); pSG5 empty vector (striped bar); and normal naive control mouse (□).
Figure 5J:
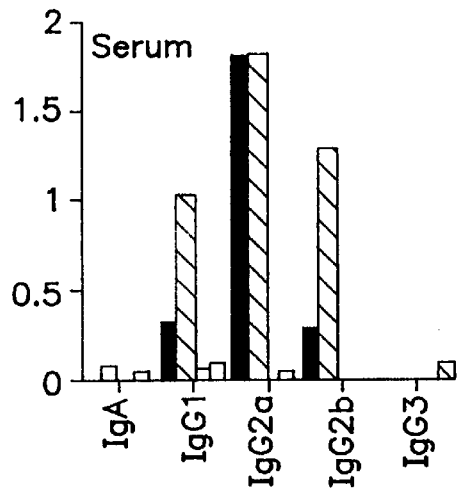
FIG. 5J is a bar graph depicting the isotypes of antirabies virus antibodies in the sera of the mice of FIG. 5I assayed at 10 weeks after priming. The symbols are the same as in FIG. 5I.
Figure 5K:
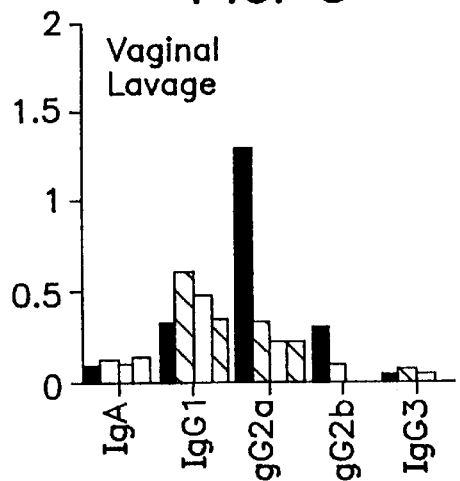
FIG. 5K is a bar graph depicting the isotypes of antirabies virus antibodies in the vaginal lavage of mice primed with a DNA vaccine to rabies virus (pSG5rab.gp) administered together with a plasmid vector encoding interleukin (IL)-5 (pcDNA3IL-5). Lavage were assayed at 4 weeks after priming. The symbols are the same as in FIG. 5I.
Figure 5L:
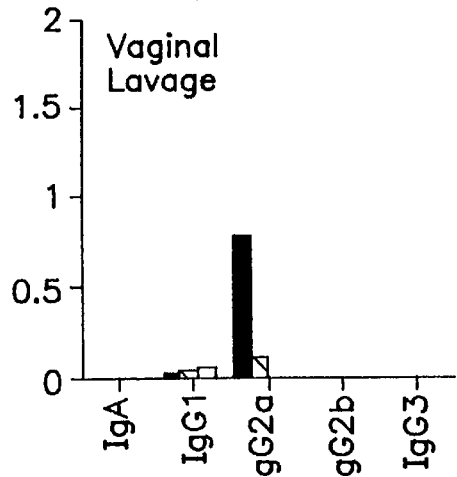
FIG. 5L is a bar graph depicting the isotypes of antirabies virus antibodies in the vaginal lavage of mice primed with a DNA vaccine to rabies virus (pSG5rab.gp) administered together with a plasmid vector encoding interleukin (IL)-5 (pcDNA3IL-5). Lavage were assayed at 10 weeks after priming. The symbols are the same as in FIG. 5I.
Figure 5M:
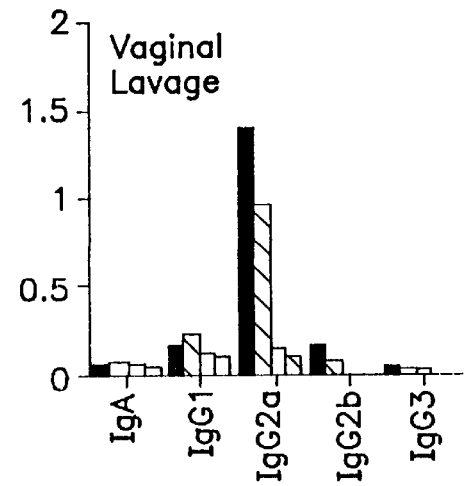
FIG. 5M is a bar graph depicting the isotypes of antirabies virus antibodies in the vaginal lavage of mice primed with a DNA vaccine to rabies virus (pSG5rab.gp) administered together with a plasmid vector encoding interleukin (IL)-5 (pcDNA3IL-5) and boosted i.n. with $2 \times 10^5$ pfu of Adrab.gp recombinant. Lavage were assayed at 5 days after boost. The symbols are pSG5rab.gp + pcDNA3IL5+Adrab.gp (□), pSG5rab.gp+Adrab.gp (striped bar), pSG5+Adrab.gp (strippled bar), pcDNA3IL-5+Adrab.gp (dotted bar); and normal naive control mouse (□).
Figure 5N:
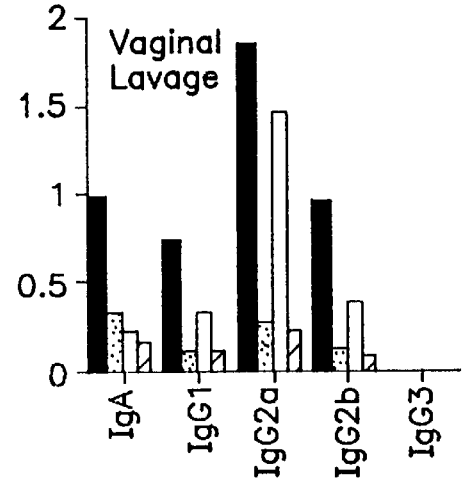
FIG. 5N is a bar graph depicting the isotypes of antirabies virus antibodies in the vaginal lavage of mice primed with a DNA vaccine to rabies virus (pSG5rab.gp) administered together with a plasmid vector encoding interleukin (IL)-5 (pcDNA3IL5) and boosted i.n. with $2 \times 10^5$ pfu of Adrab.gp recombinant. Lavage were assayed at 10 days after boost. The symbols are the same as in FIG. 5M.

As illustrated in FIGS. 5A through 5N, priming with a DNA vaccine in the presence of a genetic adjuvant (i.e., pSG5rab.gp/pcDNA3IL-5) increased the antibody titers to rabies virus present in the vaginal lavage over priming with pSG5rab.gp alone at all time points. Interestingly, co-priming with pcDNA3IL-5 did not have as marked an effect in raising serum antibody titers. Thus, co-priming with a genetic adjuvant encoding a cytokine, in this case interleukin-5, further augmented the antigen-specific mucosal immune response upon subsequent boosting with a recombinant vaccine also expressing the antigen. Further, the increased mucosal immune response induced by co-priming with pcDNA3IL-5 was observed even before boosting and was greater than the effect of co-prming on serum antibody titers.

Determination of antibody isotypes in sera and vaginal lavage demonstrated that co-priming with pcDNA3IL-5 resulted in a long-term response characterized by IgA and IgG2a isotypes. Therefore, these data demonstrate that augmentation of the mucosal immune response by DNA priming followed by intranasal booster immunization can be selectively enhanced by the use of genetic adjuvants.

EXAMPLE 5: EFFECT OF PREEXISTING IMMUNITY TO ADENOVIRUS ON PRIMING WITH A DNA VACCINE FOLLOWED BY AN ADENOVIRAL BOOSTER IMMUNIZATION

Under conditions in which the boosting vaccine uses a recombinant virus as the carrier encoding the antigen to which the immune response is desired in the immunized mammal, this example determined the effect of the methods of the present invention on mammals with pre-existing immune responses to the viral carrier. This example explored whether the priming DNA vaccine could augment the antibody response to the antigen expressed by an adenoviral recombinant in mammals with preexisting immunity to the virus carrier. Specifically, in this example, the subject mammals have preexisting immunity to wild-type adenovirus human strain 5, which forms the vaccine carrier of the Adrab.gp recombinant.

A. Protocol

An adenovirus recombinant expressing the HPV E7 gene was prepared as follows. The E7 fragment was excised from the pBlue.E7 vector [generated from the E7 open reading frame of the pBR322HPV-16 vector described in K. Seedorf et al., Virol., 145:181–185 (1985)] by NotI and XhoI digestion and blut-ended into the NotI site of the pAdCMVlacZ vector [Z. Xiang et al., Virol., 12:220–227 (1996)]. Purified adenoviral DNA human strain 5 was cut with ClaI to remove the left end of the viral genome. E1 transfected 293 cells [F. Graham et al., *J. Gen. Virol.*, 36:59–72 (1977)] were co-transfected with the cut adenoviral DNA and linearized transfer vector with the E7 sequence in correct orientation to the CMV promoter. Plaques were selected, tested for presence of E7 sequences by PCR and then sub-cloned twice more to obtain recombinant virus free of wild-type virus contamination. The resulting adenovirus recombinant is termed AdE7, or AdHPV- 16E7. The recombinant virus AdHPV-16E7 contains Ad5 m.u. 0–1, followed by the CMV enhancer/promoter, the HPV-16E7 gene, a pA site and Ad5 m.u. 9–78.4 and 86–100. This recombinant was used in the following experiment to provide the animals with preexisting immunity to adenovirus.

Groups of 5 C3H/He mice were immunized with $2 \times 10^6$ pfu of the AdE7 recombinant, prepared as described above, given i.n. to induce immunity to adenovirus. One month later, the experimental groups were administered a priming dose (50 µg) of the priming DNA vaccine pSG5rab.gp of Example 2 or the pSG5 vector lacking any rabies antigen. Both priming vaccines were administered i.m. as described in the previous examples. After two months, mice were boosted i.n. with $2 \times 10^6$ pfu of the boosting composition which used the adenovirus as the vaccine vehicle and encoded the same antigen. In this experiment, the recombinant vaccine was Adrab.gp described in the previous examples. Naive control mice were immunized i.n. at the same time with Adrab.gp. Sera and vaginal lavage were harvested 10 days later and tested for antibodies to rabies virus by the assays described in Example 1.

B. Results

Figure 6A:
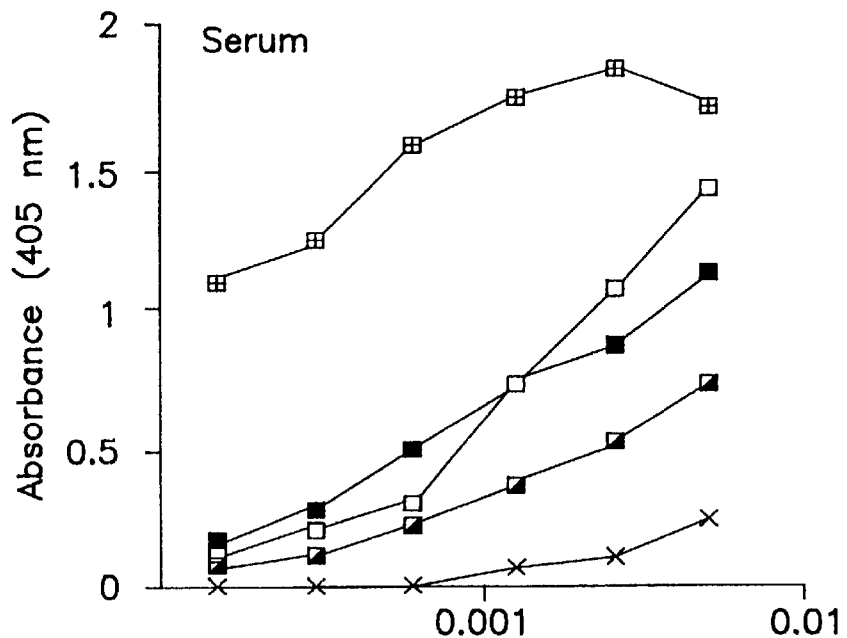
FIG. 6A is a graph illustrating the serum antibody response in mice preimmune to adenovirus. Mice were immunized with an E1-deleted adenovirus containing the E7 gene of HPV-16 in the site of the E1 deletion (AdE7) given i.n. Six weeks later, some of the mice were boosted with pSG5 or pSG5rab.gp vector given i.m. Eight weeks later, naive as well as preimmune mice were boosted with Adrab.gp virus given i.n. Sera were tested 10 days later. The symbols are as follows, ■, AdE7+pSG5rab.gp □, Adrab.gp; □, Adrab.gp only; ⊞, AdE7+pSG5rab.gp; ◢, AdE7 + Adrab.gp; (x), naive mice.
Figure 6B:
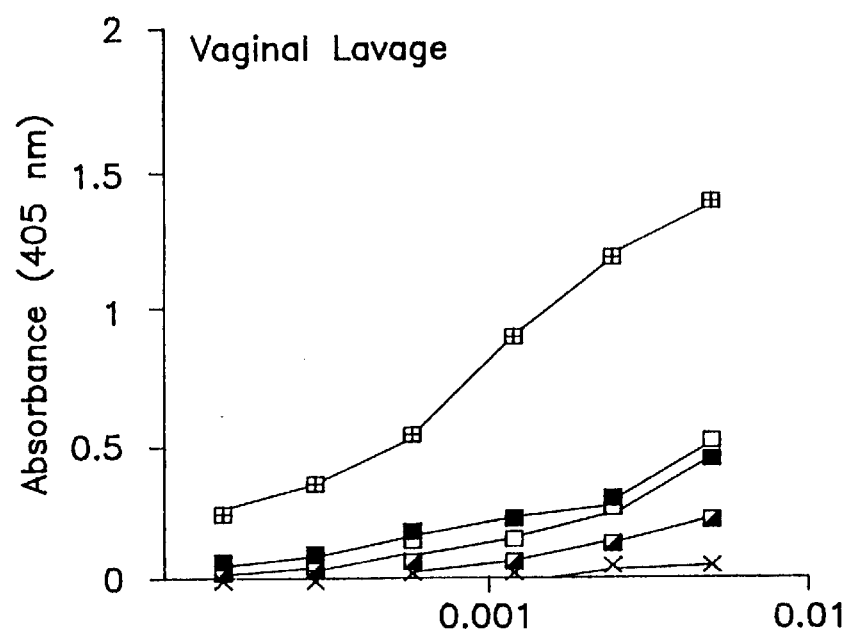
FIG. 6B is a graph illustrating the antibody response of the mice of FIG. 6A in vaginal lavage. The symbols are the same as in FIG. 6A.

As shown in FIGS. 6A and 6B, the antibody response to the rabies antigen as expressed by the adenoviral recombinant was reduced in sera of adenovirus preimmune mice, while no difference was observed in vaginal lavage. In both fluids, DNA vaccine priming strongly augmented the antibody response above that seen in naive mice vaccinated with the Adrab.gp recombinant only. Thus, the combination vaccine regimen of the present invention was suited to overcome the impairment of the antibody response to the rabies virus antigen due to preexisting immunity to the vaccine carrier.

EXAMPLE 6: INTRAMUSCULAR PRIMING WITH A DNA VACCINE AUGMENTS THE MUCOSAL IMMUNE RESPONSE UPON INTRANASAL BOOSTING WITH THE AdHPV-16L1 RECOMBINANT VIRUS

In this example, one embodiment of the vaccine method of the invention is illustrated in which a priming dose of a DNA vaccine, expressing the L1 antigen of the papilloma virus is used for priming a vaginal immune response to a boosting dose given intranasally of the adenoviral recombinant AdHPV-16L1.

A. The DNA Vaccine

An exemplary DNA vaccine is the pVRHPV16-L1 vector, which expresses a 1.48 kb sequence containing the HPV-16L1 gene under the control of the CMV promoter in the plasmid vector pVR1012.2 vector [Vical, Inc., San Diego, Calif.]. pVRHPV16-L1 was constructed by cloning the HPV16-L1 gene into the multicloning site downstrean of the CMV promoter in this vector. The kanamycin resistance gene of the original vector was replaced with the ampicillin resistance gene. This construction was similar to that of pVRrab.gp described in Example 3. This bacterial plasmid is employed as the DNA vaccine in the following protocol.

B. The Recombinant AdHPV-16L1 Adenovirus

The adenoviral recombinant expressing the human papilloma virus type 16L1 protein is prepared in the same manner as described for the Adrab.gp recombinant. The pVRHPV16-L1 plasmid is digested with SalI and HindII to free the 1.48 kb sequence of the HPV-16L1 gene, which is then inserted into NotI-digested pAd.CMV-LacZ (a 5.6kb vector missing the LacZ gene) via blunt and cloning to generate pAdCMV.HPV-16LI. The appropriate orientation of the insert is confirmed by restriction enzyme mapping. This plasmid is linearized with NheI, cotransfected into 293 packaging cells, and cultured with an E3 deleted Ad5 DNA, Ad5dl7001. The replication defective clone termed AdHPV.L1 is purified by plaque purification. AdHPV-16L1 is essentially identical to Adrab.gp, except that the heterologous insert is L1, not rabies glycoprotein. This recombinant virus contains Ad5m.u. 0–1, followed by the CMV enhancer/promoter, the HPVL1 gene, a pA site and Ad5 m.u. 9–78.4 and 86–100.

C. Protocol

Groups of 4–5 female 6–10 week old C3H/He mice are injected with 10–50 µg of the DNA vaccine composition described in part A above in 50 µl of either saline or water. The DNA vaccine composition is administered into both quadricep muscles, dividing the dose equally to reduce variability. One group of mice is primed with the DNA vaccine given directly intratracheally. Control mice are primed with a control plasmid without a gene insert. The boosting composition, AdHPV-16L1, is administered between 6 and 12 weeks later intranasally at $2 \times 10^6$ pfu per mouse by depositing 50 µl liquid containing $2 \times 10^6$ pfu on both nostrils. Sera and vaginal lavage are harvested from the mice just prior to the booster immunization and then at various times after boosting (10 days, one month, two months, and four months), and samples are prepared and assayed as described in Example 1.

D. Results

The results of the experimental protocol are expected to be consistent regardless of the dose of the plasmid vector (10 or 50 µg), the type of the vector construct, or the route of priming (intranasally versus intratracheally).

Antigen-specific T cell responses are determined by intracellular cytokine staining. For use in this assay, the L1 is synthesized using conventional methods. The immunodominant T cell epitopes are determined by testing the lymphocytes with a panel of peptides. The peptides may be purified by high pressure liquid chromatography and its sequence verified by mass spectroscopy. Typically, lymphocytes are harvested from vaginal tissue and incubated with or without peptide (2.5 µg/ml) for 5 hours in 96-well U-bottom plates (Costar, Cambridge, Mass.) at a concentration of $10^6$ cells/well in a volume of 200 µl in complete DMEM medium supplemented with 50 units/ml of human recombinant IL-2 and 1 µl/ml of Brefeldin A (Goldistop, Pharmingen, LaJolla, Calif.). After 5 hours the cells are washed once and surface stained with phycoerythrin (PE)-conjugated rat anti-mouse CD8 antibody (Boehringer Mannheim, Indianapolis, Ind.) followed by fixation/permeabilization (Cytofix/Cytoperm, Pharmingen, LaJolla, Ca.) and intracellular staining for IFN-γ, Pharmingen, LaJolla, Calif.) according to manufacturers' instructions. The results are assayed by flow cytometry. For flow cytometry, single cell suspensions are acquired and analyzed on a Coulter, or equivalent, flow cytometer. The threshold for positive and negative cells are set up on the basis of an isotype control antibody (FITC-Rat IgG1 isotype immunoglobulin, Pharmingen, LaJolla, Calif.). Un-stimulated cells or cells incubated with a control peptide are used to assess spontaneous IFN-γ production.

It is anticipated that prior to boosting, the mice have a readily detectable serum immune response and a T cell response in the spleen while titers in vaginal lavage or T cells at the genital tract are barely detectable. Booster immunization intranasally with the AdHPV.L1 booster is anticipated to augment the vaginal B and T cell response which are tested 10 days later. Mucosal immune response to WPV virus is anticipated to be clearly superior in DNA vaccine-primed mice compared with control mice.

The magnitude of the immune response to the adenoviral antigens is reversed, i.e., mice primed with the DNA vaccine to HPV develop only a marginal serum and vaginal lavage response to adenoviral antigens while unprimed AdHPV.L1 immunized mice develop a substantial response at both sites to adenovirus antigens, indicating that the pre-existing immune response to the plasmid encoded antigen actively inhibits the immune response to the vaccine carrier.

EXAMPLE 7: PRIMING WITH A GENETIC ADJUVANT CO-ADMINISTERED WITH THE DNA VACCINE FURTHER ENHANCES THE MUCOSAL RESPONSE TO BOOSTING VACCINE

This example illustrates the priming and boosting method of this invention which further augments the mucosal immune response by co-priming with a genetic adjuvant.

A. Protocol

Five groups of 4–5 female 6–10 week old C3H/He mice are treated as follows: One group of mice is primed with 10–50 μg of the DNA vaccine of pVRHPV16-L1 administered in 50 μl of either saline or water into both quadricep muscles, dividing the dose equally to reduce variability as described in Example 5. A second group of mice is primed with the same dose and using the same route of empty vector only (i.e., pVR1012.2). A third group of mice is given a combination of pVRHPV16-L1 (50 μg) with a vector encoding the genetic adjuvant interleuken-4, pcDNAIL-4 (50μg). A fourth group of mice is primed with the vector encoding the genetic adjuvant only. Finally, the fifth control group mice is not immunized at all.

The boosting composition, AdHPV-16L1, is administered to all five groups between 6 and 12 weeks later intranasally at $2\times10^6$ pfu per mouse by depositing 50 μl liquid containing $2\times10^6$ pfu on both nostrils. Sera and vaginal lavage are harvested from the mice and samples are prepared and assayed for antibody titers and isotypes at 4 and at 10 weeks after priming with the DNA vaccine(s) and again at 5 days and 10 days after boosting, as described in Example 1.

B. Results

Priming with a DNA vaccine in the presence of a genetic adjuvant (i.e., pVRHPV16-L1/pcDNAIL4) is expected to increase the antigen-specific T cell response to HPV present in the vaginal mucosa over priming with pVRHPV16-L1 alone at all time points. Co-priming with a genetic adjuvant encoding a cytokine, in this case interleukin-4, is expected to further augment the antigen-specific mucosal immune response upon subsequent boosting with a recombinant vaccine also expressing the antigen. Further, the increased mucosal immune response induced by co-priming with pcDNA3IL-4 is likely to be observed even before boosting and is greater than the effect of co-priming on non-mucosal cellular immune response.

The results of this experiment are anticipated to demonstrate that augmentation of the mucosal immune response by DNA priming followed by intranasal booster immunization can be selectively enhanced by the use of genetic adjuvants.

EXAMPLE 8: INTRAMUSCULAR PRIMING WITH A DNA VACCINE STRONGLY AUGMENTS THE MUCOSAL ANTIBODY RESPONSE UPON INTRANASAL BOOSTING WITH THE AdHPV-16E6 or AdHPV-16E7 RECOMBINANT VIRUS

In this example, one embodiment of the vaccine method of the invention is illustrated in which a priming dose of a DNA vaccine, expressing the E6 or E7 antigen of the human papilloma virus, is used for priming a vaginal immune response to a boosting dose given intranasally of the adenoviral recombinant AdHPV-16E6 or AdHPV-16E7.

A. The DNA Vaccines

One DNA vaccine employed in this example contains an about 600 bp sequence of the HPV-16E6 gene obtained from the XhoI and NotI digestion of pBlue.E6, which had been generated from the E6 open reading frame of the pBR322PHV-16 vector [Seedorf, cited above]. The XhoI-NotI digestion fragment was cloned by blunt-end ligation into the NotI site of the pAdCMVlacZ transfer vector.

Another exemplary DNA vaccine is the pVRHPV 16-E7 vector, which expresses an about 400 bp sequence containing the HPV-16E7 gene obtained from pBR322.HPV-16 vector [K. Seedorf et al., Virol., 145:181–185 (1985)] as described in Example 5, and placed under the control of the CMV promoter in the plasmid vector pVR1012.2 [Vical., Inc., San Diego, Calif.]. pVRHPV16-E7 was constructed by cloning the HPV16-E7 gene into the multicloning site downstream of the CMV promoter in this vector. The kanamycin resistance gene of the original vector was replaced with the ampicillin resistance gene. This construction was similar to that of pVRrab.gp described in Example 3. This bacterial plasmid is employed as a DNA vaccine in the following protocol.

B. The Recombinant Adenoviruses

The adenoviral recombinant expressing the human papilloma virus type 16 E6 protein is prepared in the same manner as described for AdHPV-16E7. The recombinant virus AdHPV-16E6 contains Ad5 m.u. 0–1, followed by the CMV enhancer/promoter, the HPV-16E6 gene, a pA site and Ad5 m.u. 9–78.4 and 86–100. The construction of recombinant virus AdHPV-16E7 is described in detail in Example 5.

C. Protocol

Groups of 4–5 female 6–10 week old C3H/He mice are injected with 50 μg of one of the DNA vaccine compositions described as above. The DNA vaccine compositions are administered in 50 μl of either saline or water into both quadricep muscles, dividing the dose equally to reduce variability. One group of mice are primed with each of the DNA vaccines given directly intratracheally. Control mice are primed with a control plasmid without a gene insert. The boosting compositions, AdHPV-16E6 or AdHPV-16E7, is administered between 6 and 12 weeks later intranasally at $2\times10^6$ pfu per mouse by depositing 50 µl liquid containing $2\times10^6$ pfu on both nostrils. Sera and vaginal lavage are harvested from the mice just prior to the booster immunization and then at various times after boosting (10 days, one month, two months, and four months), and samples are prepared and assayed as described in Example 1.

D. Results

The results of this experiment are expected to be analogous to those described in Example 6 above.

EXAMPLE 9: PRIMING WITH A GENETIC ADJUVANT CO-ADMINISTERED WITH THE DNA VACCINE FURTHER ENHANCES THE MUCOSAL IMMUNE RESPONSE TO BOOSTING WITH AdHPV-16E6 or AdHPV-16E7 RECOMBINANT EXPRESSING THE TARGET ANTIGEN

This example illustrates a further embodiment of the priming and boosting method of this invention, which further augments the mucosal immune response by co-priming with a genetic adjuvant.

A. Protocol

Five groups of 4–5 female 6–10 week old C3H/He mice are treated as follows: One group of mice is primed with 10–50 µg of one of the DNA vaccines of Example 8 administered in 50 µl of either saline or water into both quadricep muscles, dividing the dose equally to reduce variability. A second group of mice is primed with the same dose and using the same route with an empty vector only (i.e., without the papilloma gene). A third group of mice is given a combination of the DNA vaccine with the genetic adjuvant pcDNAIL-4 (50 µg) encoding interleukin-4. A fourth group of mice is primed with pcDNAIL-4 only. Finally, the fifth control group mice is not immunized at all.

The boosting composition, AdHPV-16E6 or AdHPV-16E7, is administered to all five groups between 6 and 12 weeks later intranasally at $2\times10^6$ pfu per mouse by depositing 50 µl liquid containing $2\times10^6$ pfu on both nostrils. Sera and vaginal lavage are harvested from the mice and samples are prepared and assayed for antibody titers and isotypes at 4 and at 10 weeks after priming with the DNA vaccine(s) and again at 5 days and 10 days after boosting, as described in Example 1.

B. Results

The results are expected to be analogous to those of Example 7.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of enhancing mammalian mucosal immunity to the repeated presentation of a viral antigen from a virus which can infect said mammal via the mucosal tissue, said method comprising the steps of:

(a) administering via an intramuscular or intradermal route of administration an effective amount of a priming DNA composition which comprises a plasmid comprising a DNA sequence encoding said viral antigen under the control of regulatory sequences directing expression thereof in a mammalian cell; and (b) subsequently administering intranasally to said mammal an effective amount of a boosting composition which comprises a recombinant adenovirus comprising a nucleotide sequence encoding said antigen under the control of a regulatory sequence directing expression thereof in a mammalian cell, wherein the immune responses induced to said antigen are enhanced in serum and at a mucosal site, and wherein mammalian immune responses to the adenovirus antigens of said recombinant adenovirus are reduced.

2. The method according to claim 1, wherein said priming DNA composition comprises a suitable physiologically acceptable carrier.

3. The method according to claim 1, wherein said effective amount of said priming composition ranges between about 1 µg to about 10,000 µg of said plasmid.

4. The method according to claim 1, wherein said priming amount is administered intramuscularly 2 to 27 weeks before administering said boosting composition.

5. The method according to claim 1, wherein said recombinant adenovirus is replication defective.

6. The method according to claim 1, wherein said mammal has pre-existing immunity to adenovirus.

7. The method according to claim 5, wherein said boosting amount ranges from about $10^4$ to about $10^{16}$ pfu of said recombinant adenovirus.

8. The method according to claim 1, wherein said virus is selected from the group consisting of a virus that causes a sexually transmitted disease, a virus that causes an upper respiratory infection, and a virus that causes an intestinal infection.

9. The method according to claim 8, wherein said virus is selected from the group consisting of herpes simplex virus types 1 and 2, human immunodeficiency virus, and human papilloma virus, and respiratory syncytial virus.

10. The method according to claim 1, wherein said method further comprises co-administeing with said priming composition a genetic adjuvant selected from a group consisting of interleukin-4, interleukin-5, and interleukin-12 expressed by a plasmid-based vector.

11. The method according to claim 10, wherein said genetic adjuvant is interleukin-5.

12. A kit for inducing mucosal immunity in mammals, said kit comprising (a) a priming composition in an intramuscular or intradermal formulation which comprises a plasmid comprising a DNA sequence encoding a viral antigen from a virus which can infect said mammal via the mucosal tissue and which is under the control of regulatory sequences directing expression thereof in a mammalian cell; (b) a boosting composition in an intranasal formulation which comprises a recombinant adenovirus comprising said DNA sequence encoding said antigen under the control of a regulatory sequence directing expression thereof in a mammalian cell; and (c) instructions for the use of said kit.

13. The kit according to claim 12, wherein said kit further comprises a composition encoding a genetic adjuvant selected from a group consisting of interleukin-4, interleukin-5, and interleukin-12.

* * * * *

UNITED STATES PATENT AND TRADEMARK OFFICE
CERTIFICATE OF CORRECTION

PATENT NO. : 6,210,663 B1
DATED : April 3, 2001
INVENTOR(S) : H. Ertl

It is certified that error appears in the above-identified patent and that said Letters Patent is hereby corrected as shown below:

Column 1,
Line 13, replace "National" with -- (National) --.
Line 40, replace "6:3279" with -- 63:3279 --.
Line 44, replace "1:462" with -- 157:3462 --.
Line 48, replace "21:3138" with -- 71:3138 --.

Column 5,
Line 3, replace "pVR1012.2 cloning vector (▦)" with -- pVR1012.2 cloning vector (◼). --.

Line 26, replace "pVR1012.2 cloning vector (◆)," with -- pVR1012.2 cloning vector (◆). --.

Column 6,
line 8, replace "vector-primed mice (◆);" with -- vector-primed (◆). -- mice Line 17, replace "vector-primed mice (◆);" with -- vector-primed mice (◆); --.

Column 7,
Line 17, replace "pcDNA3IL5 + /Adrab,gp (□)," with -- pcDNA3IL5 + Adrab.gp (◼), --.
Line 19, replace "(strippled bar)" with -- (striped bar), --.
Line 37, replace "AdE7 + pSG5rab.gp □, Adrab.gp;" with -- AdE7 + pSG5rab.gp + Adrab.gp; --.

Column 12,
Line 23, replace "Interleukin 4" with -- Interleukin-4 --.

Column 15,
Line 9, replace "J. Ep. Med. 183:1929-1935" with -- J. Exp. Med. 183:1929-1935 --.

Column 16,
Line 56, replace "12:359-367 (1991)," with -- 72:359-367(1991), --.

Column 21,
Lines 51-56, remove indentation of lines.
Line 64, replace "[Burger el al., J. Gen. Virol., 72:359-367" with -- [Burger et al., J. Gen. Virol., 72:359-367 --.

UNITED STATES PATENT AND TRADEMARK OFFICE
CERTIFICATE OF CORRECTION

PATENT NO.   : 6,210,663 B1
DATED         : April 3, 2001
INVENTOR(S)  : H. Ertl It is certified that error appears in the above-identified patent and that said Letters Patent is hereby corrected as shown below:

Column 22,
Line 19, replace "99:132-140 (1994)]." with -- 199:132-140 (1994)] --.

Column 24,
Line 29, replace "co-prming" with -- co-priming --.
Line 66, replace "12:220-227" with -- 219:220-227 --.

Column 26,
Line 10, replace "Hin-dII" with -- HindIII --.

Column 27,
Line 16, replace "WPV" with -- HPV --.
Line 31, Example 7: replace "MUCOSAL RESPONSE TO BOOSTING" WITH -- MUCOSOL IMMUNE RESPONSE TO BOOSTING --.

Column 30, claim 10,
Line 44, replace "co-administeing" with -- co-administering --.

Signed and Sealed this

Fifth Day of February, 2002

Attest:

Attesting Officer

JAMES E. ROGAN
Director of the United States Patent and Trademark Office